United States Patent [19]

Stahl et al.

[11] Patent Number: 5,844,099
[45] Date of Patent: *Dec. 1, 1998

[54] CYTOKINE ANTAGONISTS

[75] Inventors: Neil Stahl, Carmel; Aris Economides, Dobbs Ferry; George D. Yancopoulos, Yorktown Heights, all of N.Y.

[73] Assignee: Regeneron Pharmaceuticals, Inc., Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 563,105

[22] Filed: Nov. 27, 1995

Related U.S. Application Data

[60] Provisional application No. 60/006,715 Nov. 14, 1995.

Related U.S. Application Data

[63] Continuation-in-part of Ser. No. 140,222, Oct. 20, 1993, Pat. No. 5,470,952.
[51] Int. Cl.$^6$ .................. C07K 14/715; C07K 14/71; C07K 14/52; C07K 14/495
[52] U.S. Cl. .................. 530/350; 530/351; 530/402; 530/399; 424/85.2
[58] Field of Search .................. 514/2, 12; 424/85.2; 530/351, 387.1, 399, 402, 350

[56] References Cited

U.S. PATENT DOCUMENTS

| | | | |
|---|---|---|---|
| 5,262,522 | 11/1993 | Gearing | 530/350 |
| 5,426,048 | 6/1995 | Gearing | 435/252.3 |
| 5,470,952 | 11/1995 | Stahl et al. | 530/350 |
| 5,510,259 | 4/1996 | Sugamura et al. | 435/240.2 |
| 5,599,905 | 2/1997 | Mosley et al. | 530/350 |

FOREIGN PATENT DOCUMENTS

| | | | |
|---|---|---|---|
| 0 367 566 B1 | 5/1997 | European Pat. Off. | C12N 15/12 |
| WO 93/10151 | 5/1993 | WIPO . | |

OTHER PUBLICATIONS

Sato and Miyajima, Current Opinions in Cell Biology, 1994, 6:174–179.
Miayajima, et al, Annual Review of Immunology, 1992, 10:295–331.
Kondo, et al. Science, 1993, 262:1874–1877.
Hilton, et al., EMBO Journal, 1994, 13:4765–4775.
Stahl and Yancopoulos, Cell, 1993, 74:587–590.
Bassing, et al, Journal of Biological Chemistry, 1994, 269: 14861–14864.
Kotenko, et al., Journal of Biological Science, 1995, 270: 20915–20921.
Greenfeder, et al., 1995, Journal of Biological Chemistry 270:13757–13765.
Lebrun and Vale, Molecular Cell Biology, 1997, 17:1682–1691.
Kennedy and Park, Journal of Clinical Immunology,1996, 16:134–143.
Wesche, et al., Journal of Biological Chemistry, 1997, 272:7727–7731.

*Primary Examiner*—Paula K. Hutzell
*Assistant Examiner*—Robert C. Hayes
*Attorney, Agent, or Firm*—Gail Kempler

[57] ABSTRACT

Heteromeric proteins comprising a soluble α specificity determining cytokine receptor component and the extracellular domain of a β receptor component function as cytokine antagonists.

17 Claims, 21 Drawing Sheets

Fig.4.

```
         10              20              30              40              50              60
          *               *               *               *               *               *
MVTLQTWVVQALFIFLTTES  TGELLDPCGYISPESPVVQL  HSNFTAVCVLKEKCMDYFHV 70              80              90             100             110             120
          *               *               *               *               *               *
NANYIVWKTNHFTIPKEQYT  IINRTASSVTFTDIASLNIQ  LTCNILTFGQLEQNVYGITI 130             140             150             160             170             180
          *               *               *               *               *               *
ISGLPPEKPKNLSCIVNEGK  KMRCEWDGGRETHLETNFTL  KSEWATHKFADCKAKRDTPT 190             200             210             220             230             240
          *               *               *               *               *               *
SCTVDYSTVYFVNIEVWVEA  ENALGKVTSDHINFDPVYKV  KPNPPHNLSVINSEELSSIL 250             260             270             280             290             300
          *               *               *               *               *               *
KLTWTNPSIKSVIILKYNIQ  YRTKDASTWSQIPPEDTAST  RSSFTVQDLKPFTEYVFRIR 310             320             330             340             350             360
          *               *               *               *               *               *
CMKEDGKGYWSDWSEEASGI  TYEDRPSKAPSFWYKIDPSH  TQGYRTVQLVWKTLPPFEAN 370             380             390             400             410             420
          *               *               *               *               *               *
GKILDYEVTLTRWKSHLQNY  TVNATKLTVNLTNDRYLATL  TVRNLVGKSDAAVLTIPACD 430             440             450             460             470             480
          *               *               *               *               *               *
FQATHPVMDLKAFPKDNMLW  VEWTTPRESVKKYILEWCVL  SDKAPCITDWQQEDGTVHRT 490             500             510             520             530             540
          *               *               *               *               *               *
YLRGNLAESKCYLITVTPVY  ADGPGSPESIKAYLKQAPPS  KGPTVRTKKVGKNEAVLEWD 550             560             570             580             590             600
          *               *               *               *               *               *
QLPVDVQNGFIRNYTIFYRT  IIGNETAVNVDSSHTEYTLS  SLTSDTLYMVRMAAYTDEGG 610             620             630             640             650             660
          *               *               *               *               *               *
KDGPEFTFTTPKFAQGEIES  GEPKSCDKTHTCPPCPAPEL  LGGPSVFLFPPKPKDTLMIS 670             680             690             700             710             720
          *               *               *               *               *               *
RTPEVTCVVVDVSHEDPEVK  FNWYVDGVEVHNAKTKPREE  QYNSTYRVVSVLTVLHQDWL 730             740             750             760             770             780
          *               *               *               *               *               *
NGKEYKCKVSNKALPAPIEK  TISKAKGQPREPQVYTLPPS  RDELTKNQVSLTCLVKGFYP 790             800             810             820             830             840
          *               *               *               *               *               *
SDIAVEWESNGQPENNYKTT  PPVLDSDGSFFLYSKLTVDK  SRWQQGNVFSCSVMHEALHN 850             860
          *               *
HYTQKSLSLSPGKHHHHHH•
```

Fig.5.

```
              10         20             30          40             50         60
               *          *              *           *              *          *
        MVAVGCALLAALLAAPGAAL  APRRCPAQEVARGVLTSLPG  DSVTLTCPGVEPEDNATVHW 70         80             90         100            110        120
               *          *              *           *              *          *
        VLRKPAAGSHPSRWAGMGRR  LLLRSVQLHDSGNYSCYRAG  RPAGTVHLLVDVPPEEPQLS 130        140            150         160            170        180
               *          *              *           *              *          *
        CFRKSPLSNVVCEWGPRSTP  SLTTKAVLLVRKFQNSPAED  FQEPCQYSQESQKFSCQLAV 190        200            210         220            230        240
               *          *              *           *              *          *
        PEGDSSFYIVSMCVASSVGS  KFSKTQTFQGCGILQPDPPA  NITVTAVARNPRWLSVTWQD 250        260            270         280            290        300
               *          *              *           *              *          *
        PHSWNSSFYRLRFELRYRAE  RSKTFTTWMVKDLQHHCVIH  DAWSGLRHVVQLRAQEEFGQ 310        320            330         340            350        360
               *          *              *           *              *          *
        GEWSEWSPEAMGTPWTESRS  PPAENEVSTPMQALTTNKDD  DNILFRDSANATSLPVQDAG 370        380            390         400            410        420
              *†         †              *           *              *          *
        EPKSCDKTHTCPPCPAPELL  GGPSVFLFPPKPKDTLMISR  TPEVTCVVVDVSHEDPEVKF 430        440            450         460            470        480
               *          *              *           *              *          *
        NWYVDGVEVHNAKTKPREEQ  YNSTYRVVSVLTVLHQDWLN  GKEYKCKVSNKALPAPIEKT 490        500            510         520            530        540
               *          *              *           *              *          *
        ISKAKGQPREPQVYTLPPSR  DELTKNQVSLTCLVKGFYPS  DIAVEWESNGQPENNYKTTP 550        560            570         580            590
               *          *              *           *              *
        PVLDSDGSFFLYSKLTVDKS  RWQQGNVFSCSVMHEALHNH  YTQKSLSLSPGK•
```

Fig.9A.

```
              10            20            30            40            50            60
              *             *             *             *             *             *
MVTLQTWVVQALFIFLTTES TGELLDPCGYISPESPVVQL HSNFTAVCVLKEKCMDYFHV 70            80            90           100           110           120
              *             *             *             *             *             *
NANYIVWKTNHFTIPKEQYT IINRTASSVTFTDIASLNIQ LTCNILTFGQLEQNVYGITI 130           140           150           160           170           180
              *             *             *             *             *             *
ISGLPPEKPKNLSCIVNEGK KMRCEWDGGRETHLETNFTL KSEWATHKFADCKAKRDTPT 190           200           210           220           230           240
              *             *             *             *             *             *
SCTVDYSTVYFVNIEVWVEA ENALGKVTSDHINFDPVYKV KPNPPHNLSVINSEELSSIL 250           260           270           280           290           300
              *             *             *             *             *             *
KLTWTNPSIKSVIILKYNIQ YRTKDASTWSQIPPEDTAST RSSFTVQDLKPFTEYVFRIR 310           320           330           340           350           360
              *             *             *             *             *             *
CMKEDGKGYWSDWSEEASGI TYEDRPSKAPSFWYKIDPSH TQGYRTVQLVWKTLPPFEAN 370           380           390           400           410           420
              *             *             *             *             *             *
GKILDYEVTLTRWKSHLQNY TVNATKLTVNLTNDRYLATL TVRNLVGKSDAAVLTIPACD 430           440           450           460           470           480
              *             *             *             *             *             *
FQATHPVMDLKAFPKDNMLW VEWTTPRESVKKYILEWCVL SDKAPCITDWQQEDGTVHRT 490           500           510           520           530           540
              *             *             *             *             *             *
YLRGNLAESKCYLITVTPVY ADGPGSPESIKAYLKQAPPS KGPTVRTKKVGKNEAVLEWD 550           560           570           580           590           600
              *             *             *             *             *             *
QLPVDVQNGFIRNYTIFYRT IIGNETAVNVDSSHTEYTLS SLTSDTLYMVRMAAYTDEGG 610           620           630           640           650           660
              *             *             *             *             *             *
KDGPEFTFTTPKFAQGEIES GASTKGPSVFPLAPSSKSTS GGTAALGCLVKDYFPEPVTV 670           680           690           700           710           720
              *             *             *             *             *             *
SWNSGALTSGVHTFPAVLQS SGLYSLSSVVTVPSSSLGTQ TYICNVNHKPSNTKVDKKVE 730           740           750           760           770           780
              *             *             *             *             *             *
PKSCDKTHTCPPCPAPELLG GPSVFLFPPKPKDTLMISRT PEVTCVVVDVSHEDPEVKFN
```

Fig.9B.

```
          790           800           810           820           830           840
           *             *             *             *             *             *
WYVDGVEVHNAKTKPREEQY NSTYRVVSVLTVLHQDWLNG KEYKCKVSNKALPAPIEKTI 850           860           870           880           890           900
           *             *             *             *             *             *
SKAKGQPREPQVYTLPPSRD ELTKNQVSLTCLVKGFYPSD IAVEWESNGQPENNYKTTPP 910           920           930           940           950
           *             *             *             *             *
VLDSDGSFFLYSKLTVDKSR WQQGNVFSCSVMHEALHNHY TQKSLSLSPGK*
```

Fig.10.

```
          10               20              30              40              50              60
           *                *               *               *               *               *
MVTLQTWVVQALFIFLTTES TGELLDPCGYISPESPVVQL HSNFTAVCVLKEKCMDYFHV 70               80              90             100             110             120
           *                *               *               *               *               *
NANYIVWKTNHFTIPKEQYT IINRTASSVTFTDIASLNIQ LTCNILTFGQLEQNVYGITI 130              140             150             160             170             180
           *                *               *               *               *               *
ISGLPPEKPKNLSCIVNEGK KMRCEWDGGRETHLETNFTL KSEWATHKFADCKAKRDTPT 190              200             210             220             230             240
           *                *               *               *               *               *
SCTVDYSTVYFVNIEVWVEA ENALGKVTSDHINFDPVYKV KPNPPHNLSVINSEELSSIL 250              260             270             280             290             300
           *                *               *               *               *               *
KLTWTNPSIKSVIILKYNIQ YRTKDASTWSQIPPEDTAST RSSFTVQDLKPFTEYVFRIR 310              320             330
           *                *               *
CMKEDGKGYWSDWSEEASGI TYEDRPSKAPSG
```

Fig.11.

```
         10          20          30          40          50          60
          *           *           *           *           *           *
SGGQGTLVTVSSASTKGPSV FPLAPSSKSTSGGTAALGCL VKDYFPEPVTVSWNSGALTS 70          80          90         100         110         120
          *           *           *           *           *           *
GVHTFPAVLQSSGLYSLSSV VTVPSSSLGTQTYICNVNHK PSNTKVDKKVEPKSCDKTHT*
```

Fig.12.

```
          10              20              30              40              50              60
           *               *               *               *               *               *
SGASTKGPSVFPLAPCSRST SESTAALGCLVKDYFPEPVT VSWNSGALTSGVHTFPAVLQ 70              80              90             100             110             120
           *               *               *               *               *               *
SSGLYSLSSVVTVPSSSLGT KTYTCNVDHKPSNTKVDKRV ESKYGPPCPSCPAPEFLGGP 130             140             150             160             170             180
           *               *               *               *               *               *
SVFLFPPKPKDTLMISRTPE VTCVVVDVSQEDPEVQFNWY VDGVEVHNAKTKPREEQFNS 190             200             210             220             230             240
           *               *               *               *               *               *
TYRVVSVLTVLHQDWLNGKE YKCKVSNKGLPSSIEKTISK AKGQPREPQVYTLPPSQEEM 250             260             270             280             290             300
           *               *               *               *               *               *
TKNQVSLTCLVKGFYPSDIA VEWESNGQPENNYKTTPPVL DSDGSFFLYSRLTVDKSRWQ 310             320             330
           *               *               *
EGNVFSCSVMHEALHNHYTQ KSLSLSLGK*
```

Fig.13.

```
         10          20          30          40          50          60
          *           *           *           *           *           *
SGTVAAPSVFIFPPSDEQLK SGTASVVCLLNNFYPREAKV QWKVDNALQSGNSQESVTEQ 70          80          90         100
          *           *           *           *
DSKDSTYSLSSTLTLSKADY EKHKVYACEVTHQGLSSPVT KSFNRGEC*
```

Fig.14.

```
         10          20          30          40          50          60
         *           *           *           *           *           *
SGPKAAPSVTLFPPSSEELQ ANKATLVCLISDFYPGAVTV AWKADSSPVKAGVETTTPSK 70          80          90         100
         *           *           *           *
QSNNKYAASSYLSLTPEQWK SHRSYSCQVTHEGSTVEKTV APTECS*
```

Fig.15.

```
          10          20          30          40          50          60
           *           *           *           *           *           *
MVAVGCALLAALLAAPGAAL  APRRCPAQEVARGVLTSLPG  DSVTLTCPGVEPEDNATVHW 70          80          90         100         110         120
           *           *           *           *           *           *
VLRKPAAGSHPSRWAGMGRR  LLLRSVQLHDSGNYSCYRAG  RPAGTVHLLVDVPPEEPQLS 130         140         150         160         170         180
           *           *           *           *           *           *
CFRKSPLSNVVCEWGPRSTP  SLTTKAVLLVRKFQNSPAED  FQEPCQYSQESQKFSCQLAV 190         200         210         220         230         240
           *           *           *           *           *           *
PEGDSSFYIVSMCVASSVGS  KFSKTQTFQGCGILQPDPPA  NITVTAVARNPRWLSVTWQD 250         260         270         280         290         300
           *           *           *           *           *           *
PHSWNSSFYRLRFELRYRAE  RSKTFTTWMVKDLQHHCVIH  DAWSGLRHVVQLRAQEEFGQ 310         320         330         340         350         360
           *           *           *           *           *           *
GEWSEWSPEAMGTPWTESRS  PPAENEVSTPMQALTTNKDD  DNILFRDSANATSLPVQDAG
```

Fig.16.

```
            10             20             30             40             50             60
             *              *              *              *              *              *
MVAVGCALLAALLAAPGAAL  APRRCPAQEVARGVLTSLPG  DSVTLTCPGVEPEDNATVHW 70             80             90            100            110            120
             *              *              *              *              *              *
VLRKPAAGSHPSRWAGMGRR  LLLRSVQLHDSGNYSCYRAG  RPAGTVHLLVDVPPEEPQLS 130            140            150            160            170            180
             *              *              *              *              *              *
CFRKSPLSNVVCEWGPRSTP  SLTTKAVLLVRKFQNSPAED  FQEPCQYSQESQKFSCQLAV 190            200            210            220            230            240
             *              *              *              *              *              *
PEGDSSFYIVSMCVASSVGS  KFSKTQTFQGCGILQPDPPA  NITVTAVARNPRWLSVTWQD 250            260            270            280            290            300
             *              *              *              *              *              *
PHSWNSSFYRLRFELRYRAE  RSKTFTTWMVKDLQHHCVIH  DAWSGLRHVVQLRAQEEFGQ

310
             *
GEWSEWSPEAMGTTG
```

CYTOKINE ANTAGONISTS

This application is a continuation-in-part of U.S. patent application Ser. No. 08/140,222 filed Oct. 20, 1993 entitled CNTF Family Antagonists. It also claims priority of a provisional application No. 60/006,715 entitled "Heteromeric Receptors and Methods for Their Production" which was filed in the United States Patent and Trademark Office on Nov. 14, 1995.

BACKGROUND OF THE INVENTION

Although discovered for varying biological activities, ciliary neurotrophic factor (CNTF), leukemia inhibitory factor (LIF), oncostatin M (OSM) and interleukin-6 (IL-6) comprise a newly defined family of cytokines (referred to herein as the "CNTF family" of cytokines). These cytokines are grouped together because of their distant structural similarities [Bazan, J. Neuron 7: 197–208 (1991); Rose and Bruce, Proc. Natl. Acad. Sci. USA 88: 8641–8645 (1991)], and, perhaps more importantly, because they share "$\beta$" signal-transducing receptor components [Baumann, et al., J. Biol. Chem. 265:19853–19862 (1993); Davis, et al., Science 260: 1805–1808 (1993); Gearing et al., Science 255:1434–1437 (1992); Ip et al., Cell 69: 1121–1132 (1992); Stahl, et al., J. Biol. Chem. 268: 7628–7631 (1993); Stahl and Yancopoulos, Cell 74: 587–590 (1993)]. Receptor activation by this family of cytokines results from either homo- or hetero-dimerization of these $\beta$ components [Davis, et al. Science 260: 1805–1808 (1993), Murakami, et al., Science 260: 1808–1810 (1993); Stahl and Yancopoulos, Cell 74: 587–590 (1993)]. IL-6 receptor activation requires homodimerization of gp130 [Murakami, et al. Science 260: 1808–1810 (1993), Hibi, et al., Cell 63: 1149–1157 (1990)], a protein initially identified as the IL-6 signal transducer [Hibi, et al., Cell 63: 1149–1157 (1990)]. CNTF, LIF and OSM receptor activation results from heterodimerization between gp130 and a second gp130-related protein known as LIFR$\beta$ [Davis, et al., Science 260: 1805–1808 (1993)], that was initially identified by its ability to bind LIF [Gearing et al., EMBO J. 10: 2839–2848 (1991)].

In addition to the $\beta$ components, some of these cytokines also require specificity-determining "$\alpha$" components that are more limited in their tissue distribution than the $\beta$ components, and thus determine the cellular targets of the particular cytokines [Stahl and Yancopoulos, Cell 74: 587–590 (1993)]. Thus, LIF and OSM are broadly acting factors that may only require the presence of gp130 and LIFR$\beta$ on responding cells, while CNTF requires CNTFR$\alpha$ [Stahl and Yancopoulos, Cell 74: 587–590 (1993)] and IL-6 requires IL-6R$\alpha$ [Kishimoto, et al., Science 258: 593–597 (1992)]. Both CNTFR$\alpha$ (Davis et al., Science 259:1736–1739 (1993) and IL-6R$\alpha$ [Hibi, et al. Cell 63:1149–1157, Murakami, et al., Science 260:1808–1810 (1990); Taga, et al., Cell 58:573–581 (1989)] can function as soluble proteins, consistent with the notion that they do not interact with intracellular signaling molecules but that they serve to help their ligands interact with the appropriate signal transducing $\beta$ subunits [Stahl and Yancopoulos, Cell 74: 587–590 (1993)].

Additional evidence from other cytokine systems also supports the notion that dimerization provides a common mechanism by which all cytokine receptors initiate signal transduction. Growth hormone (GH) serves as perhaps the best example in this regard. Crystallographic studies have revealed that each GH molecule contains two distinct receptor binding sites, both of which are recognized by the same binding domain in the receptor, allowing a single molecule of GH to engage two receptor molecules [de Vos, et al., Science 255: 306–312 (1992)]. Dimerization occurs sequentially, with site 1 on the GH first binding to one receptor molecule, followed by the binding of site 2 to a second receptor molecule [Fuh, et al., Science 256: 1677–1680 (1992)]. Studies with the erythropoietin (EPO) receptor are also consistent with the importance of dimerization in receptor activation, as EPO receptors can be constitutively activated by a single amino acid change that introduces a cysteine residue and results in disulfide-linked homodimers [Watowich, et al., Proc. Natl. Acad. Sci. USA 89:2140–2144 (1992)].

In addition to homo- or hetero-dimerization of $\beta$ subunits as the critical step for receptor activation, a second important feature is that formation of the final receptor complex by the CNTF family of cytokines occurs through a mechanism whereby the ligand successively binds to receptor components in an ordered manner [Davis, et al. Science 260:1805–1818 (1993); Stahl and Yancopoulos, Cell 74: 587–590 (1993)]. Thus CNTF first binds to CNTFR$\alpha$, forming a complex which then binds gp130 to form an intermediate (called here the $\alpha\beta1$ intermediate) that is not signaling competent because it has only a single $\beta$ component, before finally recruiting LIFR$\beta$ to form a heterodimer of $\beta$ components which then initiates signal transduction. Although a similar intermediate containing IL-6 bound to IL-6R$\alpha$ and a single molecule of gp130 has not been directly isolated, we have postulated that it does exist by analogy to its distant relative, CNTF, as well as the fact that the final active IL-6 receptor complex recruits two gp130 monomers. Altogether, these findings led to a proposal for the structure of a generic cytokine receptor complex (FIG. 1) in which each cytokine can have up to 3 receptor binding sites: a site that binds to an optional $\alpha$ specificity-determining component ($\alpha$ site), a site that binds to the first $\beta$ signal-transducing component ($\beta1$ site), and a site that binds to the second $\beta$ signal-transducing component ($\beta2$ site) [Stahl and Yancopoulos, Cell 74: 587–590 (1993)]. These 3 sites are used in sequential fashion, with the last step in complex formation—resulting in $\beta$ component dimerization—critical for initiating signal transduction [Davis, et al. Science 260:1805–1818 (1993)]. Knowledge of the details of receptor activation and the existence of the non-functional $\beta1$ intermediate for CNTF has led to the finding that CNTF is a high affinity antagonist for IL-6 under certain circumstances, and provides the strategic basis for designing ligand or receptor-based antagonists for the CNTF family of cytokines as detailed below.

Once cytokine binding induces receptor complex formation, the dimerization of $\beta$ components activates intracellular tyrosine kinase activity that results in phosphorylation of a wide variety of substrates [Ip, et al. Cell 69:121–1132 (1992)]. This activation of tyrosine kinase appears to be critical for downstream events since inhibitors that block the tyrosine phosphorylations also prevent later events such as gene inductions [Ip, et al., Cell 69:121–1132 (1992); Nakajima and Wall, Mol. Cell. Biol. 11:1409–1418 (1991)]. Recently, we have demonstrated that a newly discovered family of non-receptor tyrosine kinases that includes Jak1, Jak2, and Tyk2 (referred to as the Jak/Tyk kinases) [Firmbach-Kraft, et al., Oncogene 5:1329–1336 (1990); Wilks, et al., Mol. Cell. Biol. 11: 2057–2065 (1991] and that are involved in signal transduction with other cytokines [Argetsinger, et al., Cell 74:237–244 (1993); Silvennoinen, et al., Proc. Natl. Acad. Sci. USA 90:8429–8433 (1993); Velazquez, et al., Cell 70: 313–322

(1992); Witthuhn, et al., Cell 74:227–236 (1993)], preassociate with the cytoplasmic domains of the β subunits gp130 and LIFRβ in the absence of ligand, and become tyrosine phosphorylated and activated upon ligand addition [Stahl et al., Science 263:92–95 (1994)]. Therefore these kinases appear to be the most proximal step of intracellular signal transduction activated inside the cell as a result of ligand binding outside of the cell. Assay systems for screening collections of small molecules for specific agonist or antagonist activities based on this system are described below.

The CNTF family of cytokines play important roles in a wide variety of physiological processes that provide potential therapeutic applications for both antagonists and agonists.

SUMMARY OF THE INVENTION

An object of the present invention is the production of IL-6 antagonists that are useful in the treatment of IL-6 related diseases or disorders.

Another object of the invention is the use of IL-6 antagonists described herein for the treatment of osteoporosis.

Another object of the invention is the use of IL-6 antagonists described herein for the treatment of both the primary and second effects of cancers, including multiple myeloma.

Yet another object of the invention is the use of IL-6 antagonists described herein for the treatment of cachexia.

Another object of the invention is the development of screening systems useful for identifying novel agonists and antagonists of members of the CNTF family of cytokines.

Another object of the invention is the development of screening systems useful for identifying small molecules that act as agonists or antagonists of the CNTF family of cytokines.

Another object of the invention is the development of other receptor based heteromeric molecules which, as with the CNTF family antagonists described herein, act as potent ligand traps for their cognate ligands.

These and other objects are achieved by the use of CNTF family receptor components, as well as components of other receptor systems that utilize heterodimeric receptors to produce nonfunctional intermediates which have both therapeutic activity as cytokine antagonists, as well as utility in assay systems useful for identifying novel agonists and antagonists of cytokines, including members of the CNTF family of ctyokines.

BRIEF DESCRIPTION OF THE FIGURES

FIG. 4. The amino acid sequence of human gp130-Fc-$His_6$. Amino acids 1 to 619 are from human gp130 (Hibi et al., Cell 63:1149–1157 (1990). Note that amino acid number 2 has been changed from a Leu to a Val in order to accommodate a Kozak sequence in the coding DNA sequence. The signal peptide of gp130-Fc-$His_6$ has been italicized (amino acids 1 to 22). The Ser-Gly bridge is shown in bold type (amino acids 620, 621). Amino acids 662 to 853 are from the Fc domain of human IgG1 (Lewis, et al., J. Immunol. 151:2829–2838 (1993). (+) mark the two cysteines (amino acids number 632 and 635) of the IgG hinge preceding the Fc that form the inter-chain disulfide bridges that link two Fc domains. The hexahistine tag is shown in bold/italic type (amino acids 854 to 859). (●) shows the position of the STOP codon.

FIG. 5. The amino acid sequence of human IL-6Rα-Fc. Key: Amino acids 1 to 358 are from human IL-6Rα (Yamasaki, et al., Science 241:825–828 (1988). Note that amino acid number 2 has been changed from a Leu to a Val in order to accommodate a Kozak sequence in the coding DNA sequence. The signal peptide of IL-6Rα-Fc has been italicized (amino acids 1 to 19). The Ala-Gly bridge is shown in bold type (amino acids 359, 360). Amino acids 361 to 592 are from the Fc domain of human IgG1 (Lewis et al., J. Immunol. 151:2829–2838 (1993). (+) mark the two cysteines (amino acids number 371 and 374) of the IgG hinge preceding the Fc that form the inter-chain disulfide bridges that link two Fc domains. (●) shows the position of the STOP codon.

FIG. 9. Amino acid sequence of gp130-Cγ1. Key: Amino acids 1 to 619 are from human gp130 (Hibi, et al., Cell 63:1149–1157 (1990). Ser-Gly bridge is shown in bold type. Amino acids 662 to 651 are from the constant region of human IgG1 (Lewis et al., J. Immunol. 151:2829–2838 (1993). (*) shows the position of the STOP codon.

FIG. 10. Amino acid sequence of gp130Δ3fibro. Key: Amino acids 1 to 330 are from human gp130 (Hibi et al., Cell 63:1149–1157 (1990). Other symbols as described in FIG. 9.

FIG. 11. Amino acid sequence of J-CH1. Key: The Ser-Gly bridge is shown in bold, the J-peptide is shown in italics, the $C_H1$ domain is underlined.

FIG. 12. Amino acid sequence of Cγ4. Key: The Ser-Gly bridge is shown in bold type. Amino acids 2 to 239 comprise the Cγ4 sequence.

FIG. 13. Amino acid sequence of κ-domain. Key: The Ser-Gly bridge is shown in bold type. Amino acids 2 to 108 comprise the κ domain. The C-terminal cysteine (amino acid 108) is that involved in the disulfide bond of the κ domain with the $C_H1$ domain of Cγ.

FIG. 14. Amino acid sequence of λ-domain. Key: The Ser-Gly bridge is shown in bold type. Amino acids 2 to 106 comprise the λ domain (Cheung, et al., J. Virol. 66: 6714–6720 (1992). The C-terminal cysteine (amino acid 106) is that involved in the disulfide bond of the λ domain with the $C_H1$ domain of Cγ.

FIG. 15. Amino acid sequence of the soluble IL-6Rα domain. Key: Amino acids 1 to 358 comprise the soluble IL-6Rα domain (Yamasaki, et al., Science 241:825–828 (1988). The Ala-Gly bridge is shown in bold type.

FIG. 16. Amino acid sequence of the soluble IL-6Rα313 domain: Key: Amino acids 1 to 313 comprise the truncated IL-6Rα domain (IL-6Rα313). The Thr-Gly bridge is shown in bold type.

DETAILED DESCRIPTION OF THE INVENTION

Figure 1:
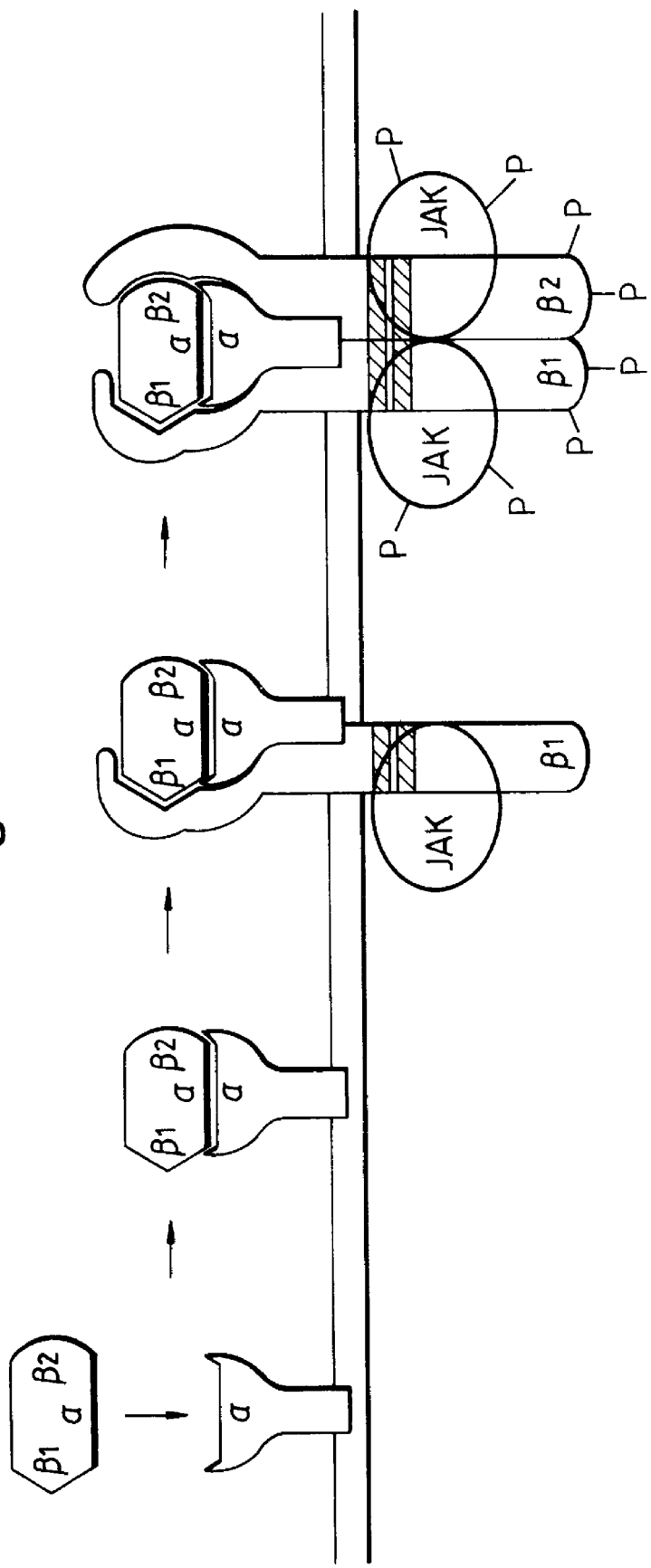
FIG. 1: Ordered binding of receptor components in a model of a generic cytokine receptor. The model indicates that cytokines contain up to 3 receptor binding sites and interact with their receptor components by binding first the optional α component, followed by binding to β1, and then β2. The β components for many cytokine receptors interact through membrane proximal regions (shaded boxes) with the Jak/Tyk family of cytoplasmic protein tyrosine kinases. Only upon dimerization of β components is signal transduction initiated, as schematized by the tyrosine phosphorylations (P) of the β components and the Jak/Tyk kinases.

The present invention provides novel antagonists which are based on receptor components that are shared by cytokines such as the CNTF family of cytokines.

The invention described herein contemplates the production of antagonists to any cytokine that utilizes an α specificity determining component which, when combined with the cytokine, binds to a first β signal transducing component to form a nonfunctional intermediate which then binds to a second β signal transducing component causing β-receptor dimerization and consequent signal transduction. According to the invention, the soluble α specificity determining component of the receptor (sRα) and the extracellular domain of the first β signal transducing component of the cytokine receptor (β1) are combined to form heterodimers (sRα:β1) that act as antagonists to the cytokine by binding the cytokine to form a nonfunctional complex.

As described in Example 1, CNTF and IL-6 share the β1 receptor component gp130. The fact that CNTF forms an intermediate with CNTFRα and gp130 can be demonstrated (Example 1) in cells lacking LIFRβ, where the complex of CNTF and CNTFRα binds gp130, and prevents homodimerization of gp130 by IL-6 and IL-6Rα, thereby blocking signal transduction. These studies provide the basis for the development of the IL-6 antagonists described herein, as they show that if, in the presence of a ligand, a nonfunctional intermediate complex, consisting of the ligand, its α receptor component and its β1 receptor component, can be formed, it will effectively block the action of the ligand. Other cytokines may use other β1 receptor components, such as LIFRβ, which may also be used to produce antagonists according to the present invention.

Thus for example, in one embodiment of the invention, effective antagonists of IL-6 or CNTF consist of heterodimers of the extracellular domains of the α specificity determining components of their receptors (sIL-6Rα and sCNTFRα respectively) and the extracellular domain of gp130. The resultant heterodimers, which are referred to hereinafter as sIL-6Rα:β1 and sCNTFRα:β1 respectively, function as high-affinity traps for IL-6 or CNTF, respectively, thus rendering the cytokine inaccessible to form a signal transducing complex with the native membrane-bound forms of their receptors.

Although soluble ligand binding domains from the extracellular portion of receptors have proven to be somewhat effective as traps for their ligands and thus act as antagonists [Bargetzi, et al., Cancer Res. 53:4010–4013 (1993);, et al., Proc. Natl. Acad. Sci. USA 89: 8616–8620 (1992); Mohler, et al., J. Immunol. 151: 1548–1561 (1993); Narazaki, et al., Blood 82: 1120–1126 (1993)], the IL-6 and CNTF receptors are unusual in that the α receptor components constitute ligand binding domains that, in concert with their ligands, function effectively in soluble form as receptor agonists [Davis, et al. Science 259:1736–1739 (1993); Taga, et al., Cell 58: 573–581 (1989)]. The sRα:β1 heterodimers prepared according to the present invention provide effective traps for their ligands, binding these ligands with affinities in the picomolar range (based on binding studies for CNTF to PC12D cells) without creating functional intermediates. The technology described herein may be applied to develop a cytokine trap for any ctyokine that utilizes an α-component that confers specificity, as well as a β component which, when bound to the α-specificity component, has a higher affinity for the cytokine than either component alone. Accordingly, antagonists according to the invention include antagonists of interleukins 1 through 5 [IL-1, Greenfeeder, et al. J. Biol. Chem. 270:13757–13765 (1995); Guo, et al. J. Biol. Chem. 270:27562–27568 (1995)], IL-2; [Taniguchi, et al. European Patent Nos. 0386289-A and 0386304-A (1990); Takeshita, et al. Science 257:379–382 (1992)]; IL-3; [Kitamura, et al. Cell 66:1165–1174 (1991)], IL-4; [Idzerda, et al. J. Exp. Med. 171:861–873 (1990)], IL-5; [Taverneir, et al. Cell 66:1175–1184 (1991)], IL-11 [(Cherel, et al. Direct Submission to EMBL/GenBank/DDBJ databases; accession No. Z38102)], interleukin 15 [IL-15; Hemar, et al. J. Cell Biol. 1295:55–64 (1995); Taniguchi, et al. European Patent Nos. 0386289-A and 0386304-A (1990); Takeshita, et al. Science 257:379–382 (1992)], granulocyte-macrophage colony stimulating factor [GM-CSF; Hayashida, et al. Proc. Natl. Acad. Sci. U.S.A. 97:9655–9659 (1990)], LIF, gamma interferon [IFNγ; Aguet, et al. Cell 55:273–280 (1988); Soh, et al. Cell 76:793–802 (1994)], and transforming growth factor beta [TGFβ; Inagaki, et al. Proc. Natl. Acad. Sci. USA 90:5359–5363 (1993)].

The α and β receptor extracellular domains may be prepared using methods known to those skilled in the art. The CNTFRα receptor has been cloned, sequenced and expressed [Davis, et al. (1991) Science 253:59–63 which is incorporated by reference in its entirety herein]. The cloning of LIFRβ and gp130 are described in Gearing et al. in EMBO J. 10:2839–2848 (1991), Hibi, et al. Cell 63:1149–1157 (1990) and in published PCT application WO 93/10151 published May 27, 1993, all of which are incorporated by reference in their entirety herein.

The receptor molecules useful for practicing the present invention may be prepared by cloning and expression in a prokaryotic or eukaryotic expression system. The recombinant receptor gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The sRα:β heterodimeric receptors may be engineered using known fusion regions, as described in published PCT application WO 93/10151 published May 27, 1993 entitled "Receptor for Oncostatin M and Leukemia Inhibitory Factor" which describes production of β receptor heterodimers, or they may be prepared by crosslinking of extracellular domains by chemical means. The domains utilized may consist of the entire extracellular domain of the α and β components, or they may consist of mutants or fragments thereof that maintain the ability to form a complex with its ligand and other components in the sRα:β1 complex. For example, as described below in example 4, IL-6 antagonists have been prepared using gp130 that is lacking its three fibronectin-like domains.

In one embodiment of the invention, the extracellular domains are engineered using leucine zippers. The leucine zipper domains of the human transcription factors c-jun and c-fos have been shown to form stable heterodimers [Busch and Sassone-Corsi, Trends Genetics 6: 36–40 (1990); Gentz, et al., Science 243: 1695–1699 (1989)] with a 1:1 stoichiometry. Although jun-jun homodimers have also been shown to form, they are about 1000-fold less stable than jun-fos heterodimers. Fos-fos homodimers have not been detected.

The leucine zipper domain of either c-jun or c-fos are fused in frame at the C-terminus of the soluble or extracellular domains of the above mentioned receptor components by genetically engineering chimeric genes. The fusions may be direct or they may employ a flexible linker domain, such as the hinge region of human IgG, or polypeptide linkers consisting of small amino acids such as glycine, serine, threonine or alanine, at various lengths and combinations. Additionally, the chimeric proteins may be tagged by His-His-His-His-His-His ($His_6$), [SEQ. ID NO. 1] to allow rapid purification by metal-chelate chromatography, and/or by epitopes to which antibodies are available, to allow for detection on western blots, immunoprecipitation, or activity depletion/blocking in bioassays.

In another embodiment, as described below in Example 3. the sRα:β1 heterodimer is prepared using a similar method, but using the Fc-domain of human IgG1 [Aruffo, et al., Cell 67:35–44 (1991)]. In contrast to the latter, formation of heterodimers must be biochemically achieved, as chimeric molecules carrying the Fc-domain will be expressed as disulfide-linked homodimers. Thus, homodimers may be reduced under conditions that favor the disruption of inter-chain disulfides but do not effect intra-chain disulfides. Then monomers with different extracellular portions are mixed in equimolar amounts and oxidized to form a mixture of homo- and heterodimers. The components of this mixture are separated by chromatographic techniques. Alternatively, the formation of this type of heterodimers may be biased by genetically engineering and expressing molecules that consist of the soluble or extracellular portion of the receptor components followed by the Fc-domain of hIgG, followed by either the c-jun or the c-fos leucine zippers described above [Kostelny, et al., J. Immunol. 148: 1547–1553 (1992) ]. Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/blocking in bioassays.

In additional embodiments, heterodimers may be prepared using other immunoglobulin derived domains that drive the formation of dimers. Such domains include, for example, the heavy chains of IgG (Cγ1 and Cγ4), as well as the constant regions of kappa (κ) and lambda (λ) light chains of human immunoglobulins. The heterodimerization of Cγ with the light chain occurs between the CH1 domain of Cγ and the constant region of the light chain ($C_L$), and is stabilized by covalent linking of the two domains via a single disulfide bridge. Accordingly, as described in Example 4, constructs may be prepared using these immunoglobulin domains. Alternatively, the immunoglobulin domains include domains that may be derived from T cell receptor components which drive dimerization, In another embodiment of the invention the sRα:β1 heterodimers are prepared by expression as chimeric molecules utilizing flexible linker loops. A DNA construct encoding the chimeric protein is designed such that it expresses two soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the order of the soluble or extracellular domains fused is switched (e.g. sIL6Rα/loop/sgp130 or sgp130/loop/sIL-6Rα) and/or in which the length and composition of the loop is varied, to allow for selection of molecules with desired characteristics.

Alternatively, the heterodimers made according to the present invention may be purified from cell lines cotransfected with the appropriate α and β components. Heterodimers may be separated from homodimers using methods available to those skilled in the art. For example, limited quantities of heterodimers may be recovered by passive elution from preparative, nondenaturing polyacrylamide gels. Alternatively, heterodimers may be purified using high pressure cation exchange chromatography. Excellent purification has been obtained using a Mono S cation exchange column.

In addition to sRα:β1 heterodimers that act as antagonists by binding free CNTF or IL-6, the present invention also contemplates the use of engineered, mutated versions of IL-6 with novel properties that allow it to bind to IL-6Rα and a single gp130 molecule, but fail to engage the second gp130 to complete β component homodimerization, and thus act as an effective IL-6 antagonist on any IL-6 responsive cell. Our model for the structure of the IL-6 and CNTF receptor complexes indicates that these cytokines have distinct sites for binding the α, β1, and β2 receptor components [Stahl and Yancopoulos, Cell 74: 587–590 (1993)]. Mutations of critical amino acid residues comprising each of these sites gives rise to novel molecules which have the desired antagonistic properties. Ablation of the β1 site would give a molecule which could still bind to the α receptor component but not the β1 component, and thereby comprise an antagonist with nanomolar affinity. Mutations of critical amino acid residues comprising the β2 site of IL-6 (IL-6β2$^-$) would give a molecule that would bind to IL-6Rα and the first gp130 monomer, but fail to engage the second gp130 and thus be functionally inactive. Similarly, mutations of the CNTF β2 site would give a molecule (CNTFβ2$^-$) that would bind CNTFRα and gp130, but fail to engage LIFRβ, thereby antagonizing CNTF action by forming the non-functional β1 intermediate. Based on the binding results described above where CNTF forms the β1 intermediate with high affinity, both CNTFβ2$^-$ and IL-6β2$^-$ would constitute antagonists with affinity in the range of 10 pM.

A variety of means are used to generate and identify mutations of IL-6 or CNTF that have the desired properties. Random mutagenesis by standard methods of the DNA encoding IL-6 or CNTF may be used, followed by analysis of the collection of products to identify mutated cytokines having the desired novel properties as outlined below. Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis [Cunningham and Wells (1989), Science 244: 1081–1085] and homolog-scanning mutagenesis [Cunningham, et al., (1989), Science 243:1330–1336].

Targeted mutagenesis of the IL-6 or CNTF nucleic acid sequences using such methods can be used to generate CNTFβ2- or IL-6β2- candidates. The choice of regions appropriate for targeted mutagenesis is done systematically, or determined from studies whereby panels of monoclonal antibodies against each factor are used to map regions of the cytokine that might be exposed after binding of the cytokine to the α receptor component alone, or to the αβ1 heterodimeric soluble receptors described above. Similarly, chemical modification or limited proteolysis of the cytokine alone or in a complex bound to the α receptor component or the αβ1 heterodimeric soluble receptors described above, followed by analysis of the protected and exposed regions could reveal potential β2 binding sites.

Assays for identifying CNTF or IL-6 mutants with the desired properties involve the ability to block with high affinity the action of IL-6 or CNTF on appropriately responsive cell lines [Davis, et al., Science 259: 1736–1739 (1993); Murakami, et al., Proc. Natl. Acad. Sci. USA 88: 11349–11353 (1991)]. Such assays include cell proliferation, survival, or DNA synthesis driven by CNTF or IL-6, or the construction of cell lines where binding of factor induces production of reporters such as CAT or β-galactosidase [Savino, et al., Proc. Natl. Acad. Sci. USA 90: 4067–4071 (1993)].

Alternatively, the properties of various mutants may be assessed with a receptor-based assay. One such assay consists of screening mutants for their ability to bind the sRα:β1 receptor heterodimers described above using epitope-tagged [Davis et al., Science 253: 59–63 (1991)] sRα:β1 reagents. Furthermore, one can probe for the presence or absence of the β2 site by assessing whether an epitope-tagged soluble β2 reagent will bind to the cytokine in the presence of the β1 heterodimer. For example, CNTF only binds to LIFRβ (the β2 component) in the presence of both CNTFRα and gp130 [Davis, et al. Science 260: 1805–1808 (1993); Stahl, et al. J. Biol. Chem. 268: 7628–7631 (1993)]. Thus a soluble LIFRβ reagent would only bind to CNTF in the presence of the soluble sRα:β1 dimer sCNTFRα:β1. For IL-6, the sRα:β1 reagent would be IL-6Rα:β1, and the probe for the β2 site would be epitope-tagged sgp130. Thus β2$^-$ mutants of CNTF would be identified as those that bound the sRα:β1 reagent, demonstrating that the α and β1 site of the cytokine were intact, yet failed to bind the β2 reagent.

In addition, the present invention provides for methods of detecting or measuring the activity of potential β2$^-$ mutants by measuring the phosphorylation of a β-receptor component or a signal transduction component selected from the group consisting of Jak1, Jak2 and Tyk2 or any other signal transduction component, such as the CLIPs, that are determined to be phosphorylated in response to a member of the CNTF family of cytokines.

A cell that expresses the signal transduction component(s) described herein may either do so naturally or be genetically engineered to do so. For example, Jak1 and Tyk-2-encoding nucleic acid sequences obtained as described in Velazquez, et al., Cell, Vol. 70:313–322 (1992), may be introduced into a cell by transduction, transfection, microinjection, electroporation, via a transgenic animal, etc., using any known method known in the art.

According to the invention, cells are exposed to a potential antagonist and the tyrosine phosphorylation of either the β-component(s) or the signal transduction component(s) are compared to the tyrosine phosphorylation of the same component(s) in the absence of the potential antagonist.

In another embodiment of the invention, the tyrosine phosphorylation that results from contacting the above cells with the potential antagonist is compared to the tyrosine phosphorylation of the same cells exposed to the parental CNTF family member. In such assays, the cell must either express the extracellular receptor (α-component) or the cells may be exposed to the test agent in the presence of the soluble receptor component. Thus, for example, in an assay system designed to identify agonists or antagonists of CNTF, the cell may express the α-component CNTFRα, the β-components gp130 and LIFRβ and a signal transducing component such as Jak1. The cell is exposed to test agents, and the tyrosine phosphorylation of either the β-components or the signal transducing component is compared to the phosphorylation pattern produced in the presence of CNTF. Alternatively, the tyrosine phosphorylation which results from exposure to a test agent is compared to the phosphorylation which occurs in the absence of the test agent. Alternatively, an assay system, for example, for IL-6 may involve exposing a cell that expresses the β-component gp130 and a signal transducing protein such as Jak1, Jak2 or Tyk2 to a test agent in conjunction with the soluble IL-6 receptor.

In another embodiment of the invention the above approaches are used to develop a method for screening for small molecule antagonists that act at various steps in the process of ligand binding, receptor complex formation, and subsequent signal transduction. Molecules that potentially interfere with ligand-receptor interactions are screened by assessing interference of complex formation between the soluble receptors and ligand as described above. Alternatively, cell-based assays in which IL-6 or CNTF induce response of a reporter gene are screened against libraries of small molecules or natural products to identify potential antagonists. Those molecules showing antagonist activity are rescreened on cell-based assays responding to other factors (such as GM-CSF or factors like Neurotrophin-3 that activate receptor tyrosine kinases) to evaluate their specificity against the CNTF/IL-6/OSM/LIF family of factors. Such cell-based screens are used to identify antagonists that inhibit any of numerous targets in the signal transduction process.

In one such assay system, the specific target for antagonists is the interaction of the Jak/Tyk family of kinases [Firmbach-Kraft, Oncogene 5: 1329–1336 (1990); Wilks, et al., Mol. Cell. Biol. 11:2057–2065 (1991)] with the receptor β subunits. As described above, LIFRβ and gp130 preassociate with members of the Jak/Tyk family of cytoplasmic protein tyrosine kinases, which become activated in response to ligand-induced β component dimerization Stahl, et al. Science 263:92–95 (1993). Thus small molecules that could enter the cell cytoplasm and disrupt the interaction between the β component and the Jak/Tyk kinase could potentially block all subsequent intracellular signaling. Such activity could be screened with an in vitro scheme that assessed the ability of small molecules to block the interaction between the relevant binding domains of purified β component and Jak/Tyk kinase. Alternatively, one could easily screen for molecules that could inhibit a yeast-based assay of β component binding to Jak/Tyk kinases using the two-hybrid interaction system [Chien, et al., Proc. Natl. Acad. Sci. 88: 9578–9582 (1991)]. In such a system, the interaction between two proteins (β component and Jak/Tyk kinase or relevant domains thereof in this example) induces production of a convenient marker such as β-galactosidase. Collections of small molecules are tested for their ability to disrupt the desired interaction without inhibiting the interaction between two control proteins. The advantage of this screen would be the requirement that the test compounds enter the cell before inhibiting the interaction between the β component and the Jak/Tyk kinase.

The CNTF family antagonists described herein either bind to, or compete with the cytokines CNTF and IL-6. Accordingly, they are useful for treating diseases or disorders mediated by CNTF or IL-6. For example, therapeutic uses of IL-6 antagonists would include the following:

1) In osteoporosis, which can be exacerbated by lowering of estrogen levels in post-menopausal women or through ovariectomy, IL-6 appears to be a critical mediator of osteoclastogenesis, leading to bone resorption [Horowitz, Science 260: 626–627 (1993); Jilka, et al., Science 257: 88–91 (1992)]. Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts [Jilka, et al. Science 257: 88–91 (1992)]. While estrogen replacement therapy is also used, there appear to be side effects that may include increased risk of endometrial and breast cancer. Thus, IL-6 antagonists as described herein would be more specific to reduce osteoclastogenesis to normal levels.

2) IL-6 appears to be directly involved in multiple myeloma by acting in either an autocrine or paracrine fashion to promote tumor formation [van Oers, et al., Ann Hematol. 66: 219–223 (1993)]. Furthermore, the elevated IL-6 levels create undesirable secondary effects such as bone resorption, hypercalcemia, and cachexia; in limited studies function-blocking antibodies to IL-6 or IL-6Ra have some efficacy [Klein, et al., Blood 78: 1198–1204 (1991); Suzuki, et al., Eur. J. Immunol. 22:1989–1993 (1992)]. Therefore, IL-6 antagonists as described herein would be beneficial for both the secondary effects as well as for inhibiting tumor growth.

3) IL-6 may be a mediator of tumor necrosis factor (TNF) that leads to cachexia associated with AIDS and cancer [Strassmann, et al., J. Clin. Invest. 89: 1681–1684 (1992)], perhaps by reducing lipoprotein lipase activity in adipose tissue [Greenberg, et al., Cancer Research 52: 4113–4116 (1992)]. Accordingly, antagonists described herein would be useful in alleviating or reducing cachexia in such patients.

Effective doses useful for treating these or other CNTF family related diseases or disorders may be determined using methods known to one skilled in the art [see, for example, Fingl, et al., The Pharmacological Basis of Therapeutics, Goodman and Gilman, eds. Macmillan Publishing Co., New York, pp. 1–46 ((1975)]. Pharmaceutical compositions for use according to the invention include the antagonists described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation (including antagonist expressing cells) prior to administration in vivo. For example, the pharmaceutical composition may comprise one or more of the antagonists in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, or microparticle-based implants.

EXAMPLE 1

CNTF Competes with IL-6 for Binding to GP130

Materials and Methods

Materials. A clone of PC12 cells that respond to IL-6 (PC12D) was obtained from DNAX. Rat CNTF was prepared as described [Masiakowski, et al., J. Neurochem. 57:1003–10012 (1991)]. IL-6 and sIL-6Rα were purchased from R & D Systems. Antisera was raised in rabbits against a peptide derived from a region near the C-terminus of gp130 (sequence: CGTEGQVERFETVGME) [SEQ. ID. NO. 2] by the method described (Stahl, et al. J. Biol. Chem. 268:7628–7631 (1993). Anti-phosphotyrosine monoclonal 4G10 was purchased from UBI, and reagents for ECL from Amersham.

Signal Transduction Assays. Plates (10 cm) of PC12D were starved in serum-free medium (RPMI 1640+ glutamine) for 1 hour, then incubated with IL-6 (50 ng/mL) +sIL-6R (1 mg/mL) in the presence or absence of added rat CNTF at the indicated concentrations for 5 minutes at 37° C. Samples were then subjected to anti-gp130 immunoprecipitation, SDS PAGE, and anti-phosphotyrosine immunoblotting as described (Stahl, et al. J. Biol. Chem. 268:7628–7631 (1993).

Results

Figure 2:
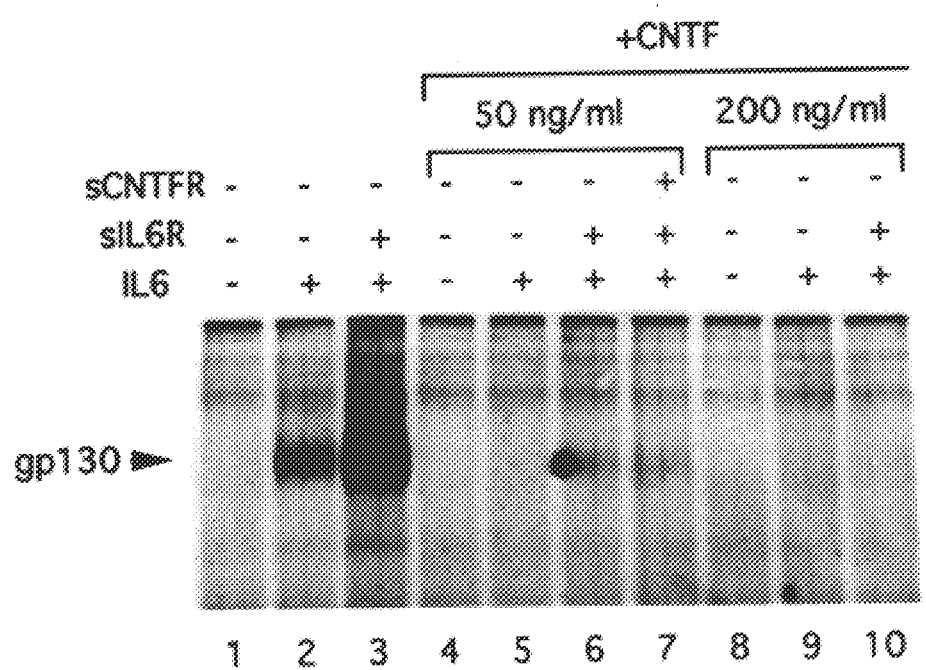
FIG. 2: CNTF inhibits IL-6 responses in a PC12 cell line (called PC12D) that expresses IL6Rα, gp130, CNTFRα, but not LIFRβ. Serum-deprived PC12D cells were incubated+ IL-6 (50 ng/mL) in the presence or absence of CNTF as indicated. Some plates also received soluble IL6Rα (1 mg/mL) or soluble CNTFRα (1 mg/mL) as indicated. Cell lysates were subjected to immunoprecipitation with anti-gp130 and immunoblotted with anti-phosphotyrosine. Tyrosine phosphorylation of gp130 is indicative of IL-6 induced activation of the IL-6 receptor system, which is blocked upon coaddition of CNTF.

The ability of CNTF to block IL-6 responses was measured using a PC12 cell line (called PC12D) that expresses IL-6Rα, gp130, and CNTFRα, but not LIFRβ. As one would predict, these cells respond to IL-6, but not to CNTF (FIG. 2) since LIFRβ is a required component for CNTF signal transduction [Davis, et al., Science 260: 59–63 (1993)]. In accordance with results on other cell lines [Ip, et al., Cell 69: 1121–1132 (1992)], PC12D cells give tyrosine phosphorylation of gp130 (as well as a variety of other proteins called CLIPs) in response to 2 nM IL-6 (FIG. 2). Addition of recombinant soluble IL-6Rα (sIL-6Rα) enhances the level of gp130 tyrosine phosphorylation, as has been reported in some other systems [(Taga, et al., Cell 58: 573–581 (1989)]. However, addition of 2 nM CNTF simultaneously with IL-6 severely diminishes the tyrosine phosphorylation of gp130. Although a slight gp130 phosphorylation response remains in the presence of CNTF, IL-6, and sIL-6Rα, it is eliminated if the CNTF concentration is increased fourfold to 8 nM. Thus, in IL-6 responsive cells that contain CNTFRα but no LIFRβ, CNTF is a rather potent antagonist of IL-6 action.

EXAMPLE 2

Binding of CNTF to the CNTFRα:β

Materials and Methods

Scatchard Analysis of CNTF Binding. $^{125}$I-CNTF was prepared and purified as described [Stahl et al. JBC 268: 7628–7631 (1993)]. Saturation binding studies were carried out in PC12 cells, using concentrations of $^{125}$I-CNTF ranging from 20 pM to 10 nM. Binding was performed directly on a monolayer of cells. Medium was removed from wells and cells were washed once with assay buffer consisting of phosphate buffered saline (PBS; pH 7.4), 0.1 mM bacitracin, 1 mM PMSF, 1 mg/ml leupeptin, and 1 mg/ml BSA. Cells were incubated in $^{125}$I-CNTF for 2 hours at room temperature, followed by 2 quick washes with assay buffer. Cells were lysed with PBS containing 1% SDS and counted in a Packard Gamma Counter at 90–95% efficiency. Nonspecific binding was defined by the presence of 100-fold excess of unlabelled CNTF. Specific binding ranged from 70% to 95%.

Results

Figure 3:
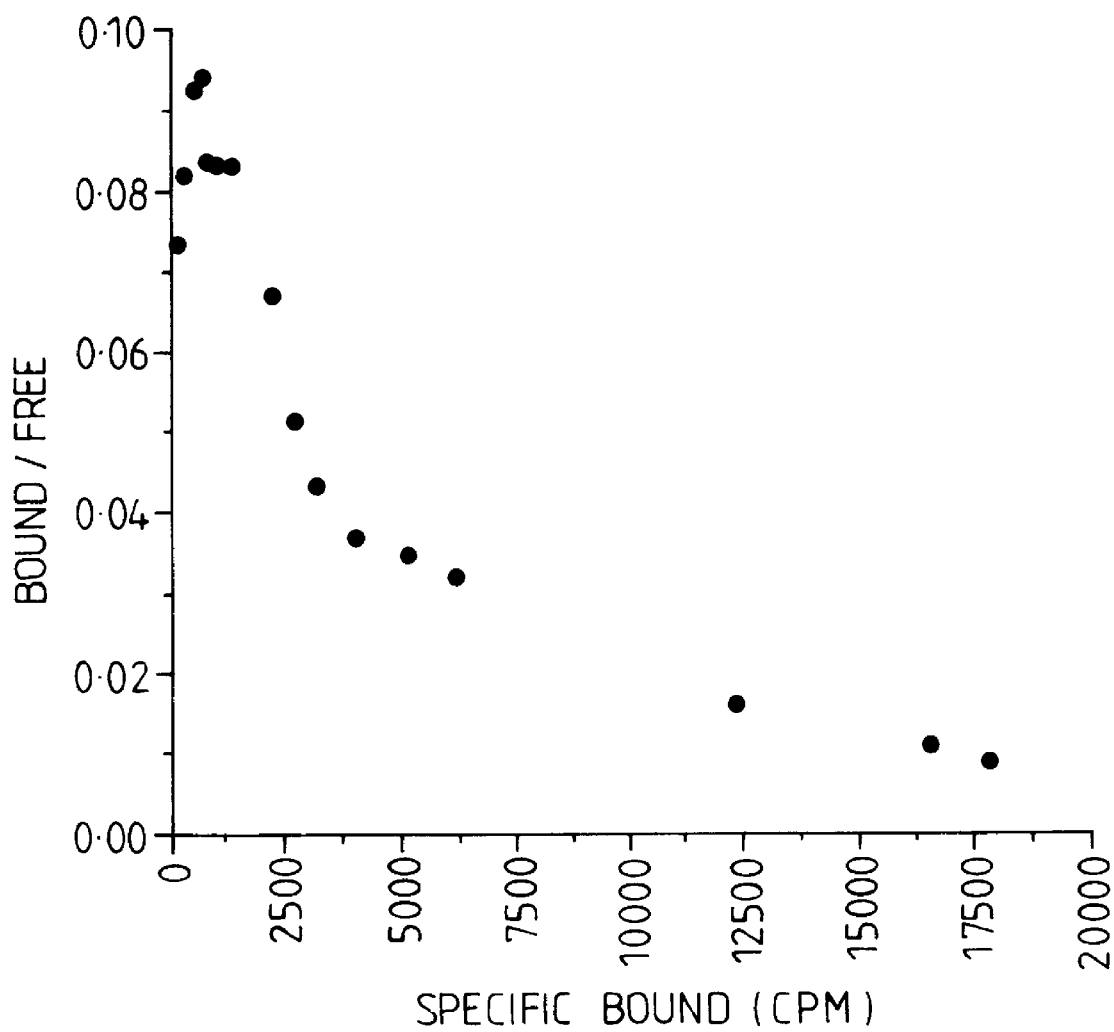
FIG. 3: Scatchard analysis of iodinated CNTF binding on PC12D cells. PC12D cells were incubated with various concentrations of iodinated CNTF in the presence or absence of excess non-radioactive competitor to determine the specific binding. The figure shows a Scatchard plot of the amount of iodinated CNTF specifically bound, and gives data consistent with two binding sites with dissociation constants of 9 pM and 3.4 nM.

The equilibrium constant for binding of CNTF to CNTFRα:β1 was estimated from Scatchard analysis of iodinated CNTF binding on PC12D cells (FIG. 3). The data is consistent with a 2 site fit having dissociation constants of 9 pM and 3.4 nM. The low affinity site corresponds to interaction of CNTF with CNTFRα, which has a Kd near 3 nM [(Panayotatos, et al., J. Biol. Chem. 268: 19000–19003 (1993)]. We interpret the high affinity complex as the intermediate containing CNTF, CNTFRα, and gp130. A Ewing sarcoma cell line (EW-1) which does contain CNTFRα, gp130, and LIFRβ, and therefore gives robust tyrosine phosphorylation in response to CNTF, displays a very similar two site fit with dissociation constants of 1 nM and 10 pM (Wong, et al., unpublished data). Thus it is apparent that CNTF binds with equally high affinity to a complex containing only CNTFRα and gp130, as it does to a complex which additionally contains LIFRβ, thus demonstrating the feasibility of creating the sRα:β antagonists described herein.

EXAMPLE 3

Methods of Producing Cytokine Ligand Traps

Virus Stock Production

SF21 insect cells obtained from *Spodoptera frugiperda* were grown at 27° C. in Gibco SF900 II medium to a density of 1×10$^6$ cells/mL. The individual virus stock for either GP130-Fc-His$_6$ (FIG. 4) or IL6Ra-Fc (FIG. 5) was added to the bioreactor to a low multiplicity 0.01–0.1 PFU/cell to begin the infection. The infection process was allowed to continue for 5–7 days allowing maximum virus replication without incurring substantial cell lysis. The cell suspension was aseptically aliquoted into sterile centrifuge bottles and the cells removed by centrifugation. The cell-free supernatant was collected in sterile bottles and stored at 4° C. until further use.

The virus titer was determined by plaque assay as described by O'Reilly, Miller and Luckow. The method is carried out in 60 mm tissue-culture dishes which are seeded with 2×10$^6$ cells. Serial dilutions of the virus stock are added to the attached cells and the mixture incubated with rocking to allow the virus to adsorb to individual cells. An agar overlay is added and plates incubated for 5–7 days at 27° C. Staining of viable cells with neutral red revealed circular plaques resulting which were counted to give the virus titer.

Coinfection of Cells for Protein Production

Uninfected SF21 Cells were grown in a 60 L ABEC bioreactor containing 40 L of SF900 II medium. Temperature was controlled at 27° C. and the dissolved oxygen level was maintained at 50% of saturation by controlling the flowrate of oxygen in the inlet gas stream. When a density of $2\times10^6$ cells/mL was reached, the cells were concentrated within the bioreactor to a volume of 20 L using a low shear steam sterilizable pump and a with tangential flow filtration device with Millipore Prostak 0.65 micron membranes. After concentration fresh sterile growth medium is slowly added to the bioreactor while the filtration system continues to remove the spent growth medium by diafiltration. After two volume exchanges (40 L) have been carried out an additional 20 L of fresh medium was added to the bioreactor to resuspend the cells to the original volume of 40 L. The cell density was determined once again by counting viable cells using a hemacytometer.

The required amount of each virus stock was calculated based on the cell density, virus titer and the desired multiplicity of infection (MOI). Virus stock ratios of 5:1, 5:2, 10:2 and 10:4, IL6Ra-Fc to GP130-Fc-$His_6$ all resulted in production of significant amounts of heterodimer. The ideal virus stock ratio is highly dependent on the ease of purification of the heterodimer from each of the two homodimers. The IL6Ra-Fc homodimer is relatively easy to remove downstream by immobilized metal affinity chromatography. Virus infection ratios have been chosen to minimize the formation of the GP130-Fc-$His_6$ homodimer which is more difficult to clear downstream. The relative amount of GP130-Fc-$His_6$ virus stock chosen for infection has increased with successive batches as the purification method for clearing the resultant homodimer has improved.

The virus stocks were aseptically mixed in a single vessel then transferred to the bioreactor. This results in synchronous infection of the SF21 cells. The infection is allowed to proceed for three to four days, allowing sufficient time for maximal production of the heterodimer protein.

Recovery and Protein A Chromatographic Purification

At the conclusion of the infection phase of the bioreactor process the cells were concentrated in the bioreactor using a 10 $ft^2$ Millipore Prostak filter (0.65 micron) pore size. The cell-free permeate passing through the filter was collected in a clean process vessel. At the conclusion of the filtration operation the pH of permeate stream, containing the protein product, was adjusted to 8.0 with 10N NaOH. The resultant precipitate was removed by forcing the extract through a 0.8 micron depth filter (Sartorious), followed by a 0.2 micron filter. Sufficient 0.5M EDTA stock was added to give a final concentration of 5 mM. The filtered protein solution was loaded onto a 10 cm diameter column containing 100–200 mL of Pharmacia Protein A Sepharose 4 Fast Flow, equilibrated with PBS. Protein A has a very high affinity for the Fc—Fc domain of each of the 3 recombinant protein products, allowing them to bind while other proteins in the cell-free extract flow through the column. After loading the column was washed to baseline with PBS containing an additional 350 mM NaCl. The IgG-Fc tagged proteins were eluted at low pH, either with 0.5M acetic acid or with a decreasing pH gradient of 0.1M citric acid and 0.2M disodium phosphate buffers. Tris base or disodium phosphate was added to the eluted protein to avoid prolonged exposure to low pH conditions.

The pooled protein was diafiltered into PBS or HEPES buffer for subsequent and derivitized with 1 mM iodoacetamide to protect the exposed sulfydryl group on the free cysteine near the hinge region of each Fc domain. This prevents disulfide mediated aggregation of proteins. A 6 ft2 Millipore spiral wound ultrafiltration membrane with nominal 30 kiloDalton cutoff was used to perform the buffer exchange. The total protein was determined by UV absorbance at 280 nm using the diafiltration buffer as a blank. The relative amounts of heterodimer and two homodimer proteins were determined by SDS PAGE gel electrophoresis using a 6% Tris-Glycine gel (Novex). Gels were Coomasie stained then transferred into destain solution overnight. A Shimadzu scanning densitometer was used to determine the relative intensity of the individual protein bands on the SDS PAGE gel. The peak area ratios are used to compute the fraction of heterodimer and each of the homodimers in the column pool fractions.

Immobilized Metal Affinity Chromatographic Purification

The six histidine residues on the C-terminus of the GP130-Fc-$His_6$ fusion protein provides an excellent molecular handle for separation of the heterodimeric IL6 antagonist from the two homodimers. The imidazole group on each of the C-terminal histidines of the GP130-Fc-$His_6$ moiety has a strong binding constant with several divalent metals, including copper, nickel, zinc, cobalt, iron and calcium. Since the IL6Ra-Fc homodimer has no C-terminal histidine residues, it clearly has the lowest affinity. The IL6Ra-Fc-GP130-Fc-$His_6$ heterodimer has a single stand set six histidines giving it greater affinity for the metal, while the GP130-Fc-$His_6$ homodimer has two sets of six histidines each giving it the highest affinity of the three IgG tagged proteins to the metal affinity column. Selective elution of the three proteins with increasing amounts of imidazole in the elution buffer therefore elutes the proteins in the following order:

1. IL6Ra-Fc homodimer
2. IL6Ra-Fc-GP130-Fc-His heterodimer
3. GP130-Fc-His homodimer A 26 mm diameter column containing 100 mL of Pharmacia Chelating Sepharose Fast Flow was saturated with a solution of nickel sulfate until a significant green color is observed in the column eluate. The column is then washed with several column volumes of deionized water, then equilibrated with 50 mM HEPES, 40 mM imidazole, pH 8.0. The binding of imidazole to the immobilized nickel results in a green to blue color change. Imidazole was added to the protein load to a final concentration of 40 mM. Addition of imidazole to the protein load reduces the binding of IL6Ra-Fc homodimer, increasing the surface area available for the remaining two species. After loading, the column was washed with several column volumes of 50 mM HEPES, 80 mM imidazole, pH 8.0 until a steady baseline was reestablished. The heterodimer was selectively eluted with 50 mM HEPES, 150 mM imidazole, pH 8.0 over several column volumes. The protein fractions were pooled and diafiltered into PBS as described in the section above.

EXAMPLE 4

Alternative Methods of Constructing Ligand Traps

Background

Figure 6:
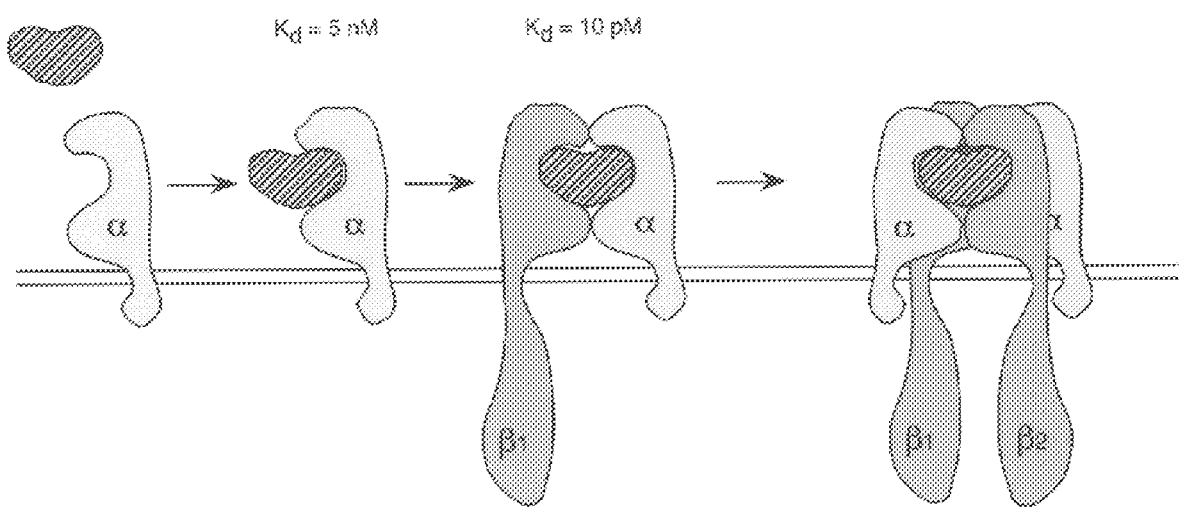
FIG. 6: The CNTF/IL-6/IL-11 receptor system. The ordered formation of the hexameric signal transducing receptor complex is depicted schematically. The cytokine associates with the Rα component to form an obligatory cytokine●Rα complex (Kd is about 5 nM). This low affinity complex next associates with the first signal transducing component, marked β1, to form a high affinity cytokine●Rα●β1 complex (Kd is about 10 pM). In the case of IL-6Rα, this component is gp130. This trimeric high affinity complex subsequently associates with another such complex. Formation of this complex results in signal transduction as it involves dimerization of two signal transducing components, marked β1 and β2 respectively (adapted from (Ward et al., J. Bio. Chem. 269:23286–23289 (1994); Stahl and Yancopoulos, J. Neurobiology 25:1454–1466 (1994); Stahl and Yancopoulos, Cell 74:587–590 (1993).

As described above, receptor activation by CNTF, and analogously by IL-6 and IL-11, follows an ordered sequence of binding events (FIG. 6). The cytokine initially binds to its cognate Rα with low affinity (Kd=3 to 10 nM); this is a required step—cells which do not express the cognate Rα do not respond to the cognate cytokine. The cytokine●Rα complex associates with the first signal transducing component, gp130, to form a high affinity complex (Kd in the order of 10 pM for the CNTF●CNTFRα●gp130 complex). This complex does not transduce signal, as it is the dimerization of the signal transducing components that brings about signaling (Stahl and Yancopoulos, J. Neurobiology 25: 1454–1466 (1994); Stahl et al., Science 267:1349–1353 (1995); Davis et al., Science 260:1805–1808 (1993); Stahl et al., Science 263:92–95 (1994); Murakami, et al. Science 260:1808–1810 (1993). At least in the case of IL-6, the cytokine●Rα●signal transducer heterotrimeric complex subsequently associates with another like complex, to form a hexameric complex (FIG. 6) (Ward et al., J. Biol. Chem. 269:23286–23289 (1994). The resulting dimerization of the signal transducers—gp130 in the case of IL-6 (Murakami et al., Science 260:1808–1810 (1993) and IL-11, gp130 and LIFR in the case of CNTF (Davis et al., Science 260:1805–1808 (1993)—brings about signal transduction.

Figure 7:
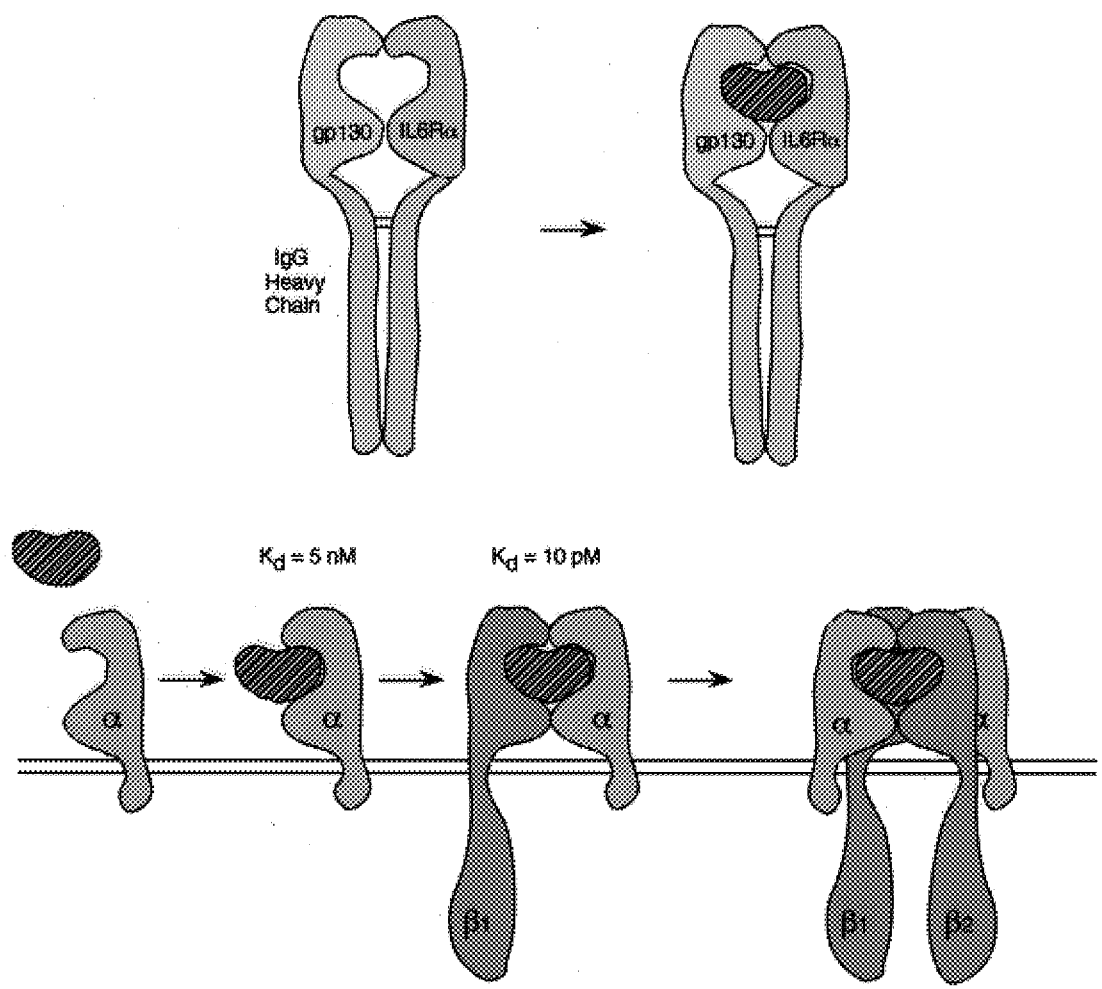
FIG. 7: Design of heterodimeric receptor-based ligand traps for IL-6. The heterodimeric ligand trap is comprised of two interdisulfide linked proteins, gp130-Fc and IL-6Rα-Fc. The gp130-Fc●IL-6Rα-Fc complex (upper panel) is shown to mimic the high affinity cytokine●Rα●β1 complex (lower panel). The ligand trap functions as an antagonist by sequestering IL-6 and thus rendering unavailable to interact with the native receptors on IL-6-responsive cells.

The initial heterodimeric molecules made comprised a soluble Rα-component linked to the extracellular domain of gp130. These molecules were shown to mimic the high affinity cytokine●Rα●gp130 complex and behave as a high affinity antagonist of their cognate cytokine (FIG. 7). To make these molecules, the extracellular domain of gp130 was paired with the extracellular domain of the α-receptor components for IL-6 and CNTF, IL-6Rα and CNTFRα respectively. To link the Rα with the extracellular domain of gp130, the soluble Rα-components and gp130 were fused to the Fc portion of human IgG1 to produce Rα-Fc and gp130-Fc respectively. The Fc domain was chosen primarily but not solely because it naturally forms disulfide-linked dimers. Heterodimeric molecules comprising Rα-Fc●gp130-Fc were expressed, purified and shown to behave as highly potent antagonists of their cognate ligand. Furthermore, these molecules were found to be highly specific for their cognate cytokine since it is the choice of the α-receptor component which specifies which cytokine is bound and trapped (there is no measurable binding of the cytokine to gp130 in the absence of the appropriate Rα).

Here we describe an extension of this technology which allows the engineering of different heteromeric soluble receptor ligand traps which by virtue of their design may have additional beneficial characteristics such as stability, Fc-receptor-mediated clearance, or reduced effector functions (such as complement fixation). Furthermore, the technology described should prove suitable for the engineering of any heteromeric protein in mammalian or other suitable protein expression systems, including but not limited to heteromeric molecules which employ receptors, ligands, and catalytic components such as enzymes or catalytic antibodies.

Materials and Methods

Genetic Engineering of Heteromeric Immunoglobulin Heavy/Light Chain Soluble Receptor-Based Ligand Traps for IL-6

Figure 8:
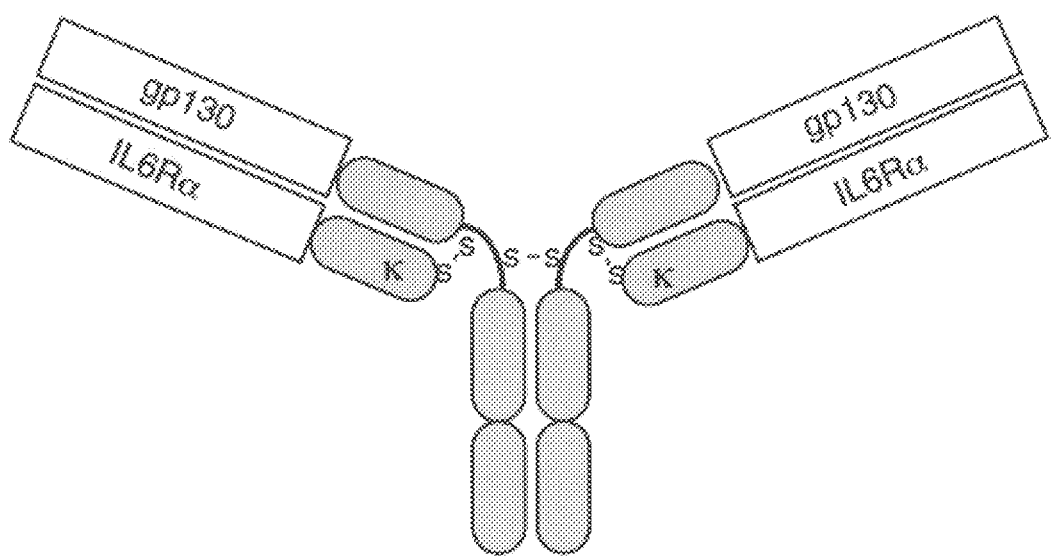
FIG. 8. Heteromeric immunoglobulin Heavy/Light Chain Receptor Fusions. An example of a heavy/light chain receptor fusion molecule is schematically depicted. The extracellular domain of gp130 is fused to Cγ, whereas the extracellular domain of IL-6Rα is fused to the constant region of the kappa chain (κ). The inter-chain disulfide bridges are also depicted (S—S).

The IL-6 traps described here were engineered using human gp130, human IL-6 α-receptor (IL-6Rα), the constant region of the heavy chains (Cγ) of human IgG1 (Cγ1) (Lewis et al., Journal of Immunology 151:2829–2838 (1993) or IgG4 (Cγ4) with or without a join-region (J), and the constant regions of kappa (κ) and lambda (λ) (Cheung, et al., Journal of Virology 66:6714–6720 (1992) light chains of human immunoglobulin (Ig), also with or without a different j-peptide (j). This design takes advantage of the natural ability of the Cγ domain to heterodimerize with κ or λ light chains. The heterodimerization of Cγ with the light chain occurs between the CH1 domain of Cγ and the constant region of the light chain ($C_L$), and is stabilized by covalent linking of the two domains via a single disulfide bridge. We reasoned that, like the Fc domain of human IgG1, the combination of Cγ with $C_L$ could be used to produce disulfide linked heteromeric proteins comprised of the extracellular domain of gp130 on one chain and the extracellular domain of IL-6Rα on the other chain. Like their Fc-based counterparts, such proteins were postulated to be high affinity ligand traps for IL-6 and as a result to inhibit the interaction of IL-6 with the native receptor on IL-6-responsive cells, thus functioning as IL-6 antagonists. Furthermore, constructs employing the full length Cγ region would, much like antibodies, form homodimers of the Cγ chain, giving rise to antibody-like molecules comprising of two "light chains" and two "heavy chains" (FIG. 8). The potential advantage of this design is that it may more closely mimic the IL-6●IL-6Rα●gp130 complex and may display a higher affinity for the ligand than comparable single heterodimers. An additional design is incorporated by using truncated versions of Cγ, comprised only of the $C_H1$ domain. These will form heterodimeric molecules with receptor-κ fusion proteins, and will thus resemble the Fab fragment of antibodies.

All the soluble receptor-Ig chimeric genes may be engineered in plasmid vectors including, but not limited to, vectors suitable for mammalian expression (Cos monkey kidney cells, Chinese Hamster Ovary cells [CHO], and ras-transformed fibroblasts [MG-ras]) and include a Kozak sequence (CGC CGC CAC CAT GGT G) at the beginning of each chimeric gene for efficient translation. Engineering was performed using standard genetic engineering methodology. Each construct was verified by DNA sequencing, mammalian expression followed by western blotting with suitable antibodies, biophysical assays that determine ligand binding and dissociation, and by growth inhibition assays (XG-1, as described later). Since the domains utilized to engineer these chimeric proteins are flanked by appropriate restriction sites, it is possible to use these domains to engineer other chimeric proteins, including chimeras employing the extracellular domains of the receptors for factors such as IL-1, IL-2, IL-3, IL-4, IL-5, GM-CSF, LIF, IL-11, IL-15, IFNγ, TGFβ, and others. The amino acid coordinates for each component utilized in making the IL-6 traps are listed below (Note: numbering starts with the initiating methionine as #1; long sequences are listed using the single letter code for the twenty amino acids):

(a) Constructs employing human gp130:

(i) gp130-Cγ1 was engineered by fusing in frame the extracellular domain of gp130 (amino acids 1 to 619) to a Ser-Gly bridge, followed by the 330 amino acids which comprise Cγ1 and a termination codon (FIG. 9).

(ii) gp130-J-Cγ1 was engineered in the same manner as gp130-Cγ1 except that a J-peptide (amino acid sequence: GQGTLVTVSS) was inserted between the Ser-Gly bridge and the sequence of Cγ1 (see FIG. 9).

(iii) gp130Δ3fibro-Cγ1 was engineered by fusing in frame the extracellular domain of gp130 without its three fibronectin-like domains (FIG. 10). The remaining part of this chimeric protein is identical to gp130-Cγ1.

(iv) gp130-J-$C_H1$ was engineered in a manner identical for that described for gp130-Cγ1, except that in place of the Cγ1 region only the $C_H1$ part of Cγ1 has been used (FIG.

11). The C-terminal domain of this construct includes the part of the hinge that contains the cysteine residue responsible for heterodimerization of the heavy chain of IgG with a light chain. The part of the hinge that contains the two cysteines involved in Cγ1 homodimerization has been deleted along with the $C_H2$ and $C_H3$ domains.

(v) gp130-Cγ4 was engineered in a manner identical to that described for gp130-Cγ1, except that Cγ4 was used in place of Cγ1 (FIG. 12). In addition, an RsrII DNA restriction site was engineered at the hinge region of the Cγ4 domain by introducing two silent base mutations. The RsrsII site allows for other desired genetic engineering manipulations, such as the construction of the $C_H1$ equivalent of gp130-Cγ4.

(vi) gp130-κ was engineered in a manner identical to that described for gp130-Cγ1, except that the constant region of the κ light chain of human Ig was used in place of Cγ1 (FIG. 13).

(vi) gp130-J-κ was engineered in a manner identical to that described for gp130-J-κ, except that a j-peptide (amino acid sequence: TFGQGTKVEIK) was inserted between the Ser-Gly bridge and the κ-region.

(viii) gp130-λ was engineered in a manner identical to that described for gp130-Cγ1, except that the constant region of the λ light chain (Cheung, et al., Journal of Virology 66:6714–6720 (1992) of human Ig was used in place of Cγ1 (FIG. 14).

Constructs employing human IL-6Ra:

(i) IL6R-Cγ1 was engineered by fusing in frame amino acids 1 to 358 of IL-6Rα (Yamasaki et al., Science 241:825–828 (1988), which comprise the extracellular domain of IL-6Rα (FIG. 15), to an Ala-Gly bridge, followed by the 330 amino acids which comprise Cγ1 and a termination codon.

(ii) IL6R-κ was engineered as described for IL6R-Cγ1, except that the κ-domain (FIG. 13) utilized for gp130-κ was used in place of Cγ1.

(iii) IL6R-j-κ was engineered as described for IL6R-κ except that the j-peptide described for gp130-j-κ was placed between the Ala-Gly bridge and the κ-domain.

(iv) Three additional constructs, IL6R313-Cγ1, IL6R313-κ, and IL6R313-j-κ, were engineered as using a truncated form of IL-6Ra comprised of amino acids 1 to 313 (FIG. 16). Each of these constructs were made by fusing in frame IL6R313 with a Thr-Gly bridge followed by the Cγ1, κ-, and j-κ-domains described above. These constructs were engineered in order to complement the gp130Δ3fibro-derived constructs.

Expression and Purification of Ligand Traps

To produce covalently linked heterodimers of soluble gp130 and soluble IL-6Rα, gp130-Ig chimeric proteins were co-expressed with appropriate IL-6Rα-Ig chimeric proteins in complementing pairs. Co-expression was achieved by co-transfecting the corresponding expression vectors into suitable mammalian cell lines, either stably or transiently. The resulting disulfide-linked heterodimers were purified from conditioned media by several different methods, including but not limited to affinity chromatography on immobilized Protein A or Protein G, ligand-based affinity chromatography, ion exchange, and gel filtration.

Figure 17:
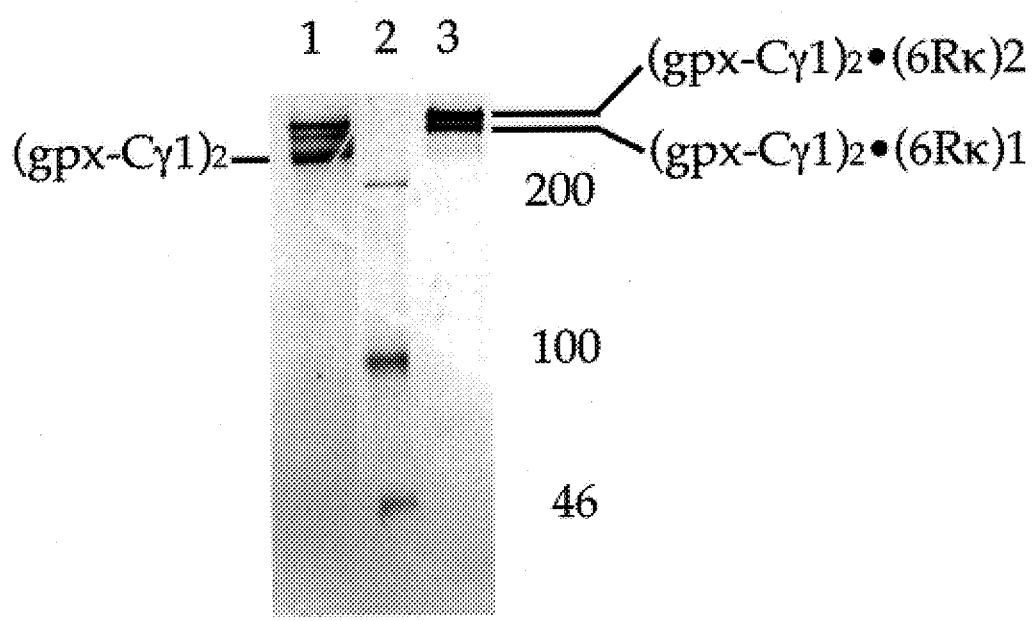
FIG. 17: Purification of gp130-Cγ1●IL-6Rα-κ. 4% to 12% SDS-PAGE gradient gel run under non-reducing conditions. Proteins were visualized by staining with silver. Lane 1: approximately 100 ng of material purified over Protein A Sepharose (Pharmacia). Lane 2: Molecular size standards (Amersham). Lane 3: The Protein A-purified material shown here after further purification over an IL-6 affinity chromatography step. The positions of the gp130-Cγ1 dimer [(gp130-Cγ1)$_2$], the gp130-Cγ1 dimer associated with one IL-6Rα-κ[(gp130-Cγ1)$_2$●(IL-6Rα-κ)$_1$], and the gp130-Cγ1 dimer associated with two IL-6Rα-κ[(gp130-Cγ1)$_2$●(IL-6Rα-κ)$_2$] are shown, as well as the sizes for the molecular size standards in kilodaltons (200, 100, and 46).

An example of the type of methods used for purification of a heavy/light receptor fusion protein is as follows: gp130-Cγ1●IL-6Rα-κ was expressed in COS cells by co-transfecting two different vectors, encoding gp130-Cγ1 and IL-6Rα-κ respectively. Serum-free conditioned media (400 ml) were collected two days post-transfection and Cγ1-bearing proteins were purified by affinity chromatography over a 1 ml Protein A Sepharose (Pharmacia). The material generated in this step was further purified by a second affinity chromatography step over a 1 ml NHS-activated Sepharose (Pharmacia) which was derivatized with recombinant human IL-6, in order to remove gp130-Cγ1 dimer from gp130-Cγ1●IL-6Rα-κ complexes (the gp130-Cγ1 dimer does not bind IL-6). Proteins generated by this method were more than 90% pure, as evidenced by SDS-PAGE followed by silver-staining (FIG. 17). Similar protocols have been employed successfully towards the purification of other heavy/light receptor heterodimers.

Results

Figure 18:
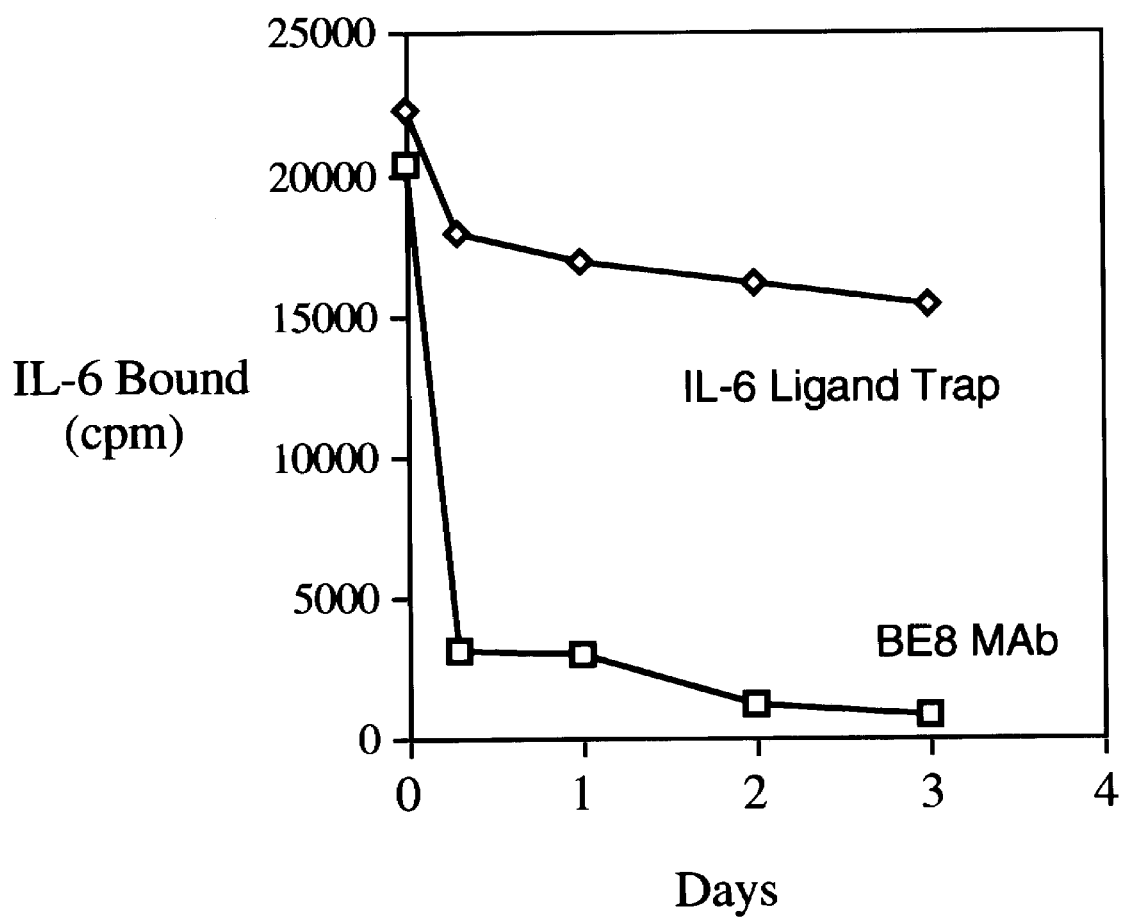
FIG. 18. IL-6 dissociates slowly from the ligand trap. The dissociation rate of IL-6 from a heavy/light chain receptor-based ligand trap (gp130-Cγ1●IL-6Rα-κ) was compared to that obtained with the neutralizing monoclonal antibody B-E8 (BE8 MAb).
Figure 19A:
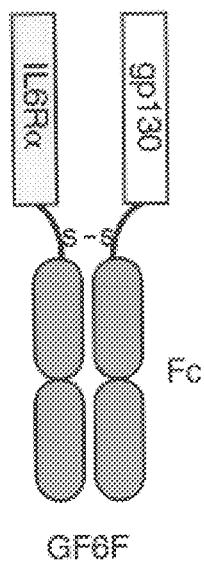
FIG. 19. IL-6 can induce multimerization of the ligand trap. (A) Two different ligand traps are depicted schematically and listed according to their ability to bind protein A. gp130-Fc●IL-6Rα-Fc (GF6F) binds protein A via its Fc-domains, whereas gp130-$C_H1$●IL-6Rα-κ (G16K) does not bind to protein A. (B) Anti-kappa western blotting of proteins precipitated with Protein A-Sepharose from mixtures of GF6F±IL-6, G16K±IL-6, or GF6F plus G16K±IL-6, as marked.
Figure 19B:
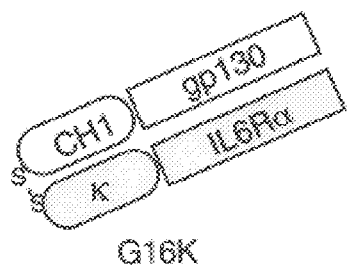
Figure 19C:
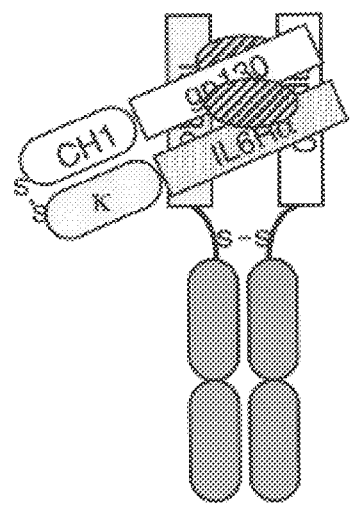
Figure 19D:
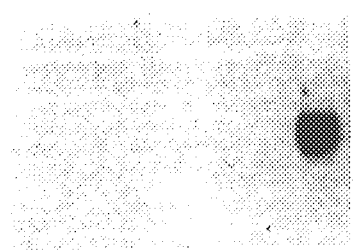

Biological Activity of Immunoglobulin Heavy/Light Chain Receptor Fusion Antagonists The purified ligand traps were tested for their ability to bind IL-6 in a variety of different assays. For example, the dissociation rate of IL-6 bound to the ligand trap was measured in parallel with the dissociation rate of IL-6 from the anti-IL-6 monoclonal neutralizing antibody B-E8 [Brochier, et al., Int. J. Immunopharmacology 17:41–48 (1995), and references within]. An example of this type of experiment is shown In FIG. 18. In this experiment 20 pM $^{125}$I-IL-6 (1000 Ci/mmol; Amersham) was preincubated with 500 pM of either gp130-Cγ1●IL-6Rα-κ or mAb B-E8 for 20 hours. At this point a 1000-fold excess (20 nM) of "cold" IL-6 was added. Periodically, aliquots of the reaction were removed, the ligand trap or B-E8 were precipitated with Protein G-Sepharose, and the number of cpm of $^{125}$I-IL-6 that remained bound was determined. Clearly, the dissociation rate of human $^{125}$I-IL6 from the ligand trap was very slow—after three days, approximately 75% of the initial counts were still bound to the ligand trap. In contrast, less than 5% of the counts remained associated with the antibody after three days. This result demonstrates that the dissociation rate of the ligand from these ligand traps is very slow.

In a different set of experiments the ability of the ligand traps to multimerize in the presence of ligand was tested. An example of this is shown on FIG. 19. IL-6-induced association of gp130-Fc●IL-6Rα-Fc with gp130-$C_H1$●IL-6Rα-κ was determined by testing whether gp130-$C_H1$●IL-6Rα-κ, which does not by itself bind protein A, could be precipitated by protein A-Sepharose in the presence of gp130-Fc●IL-6Rα-Fc in an IL-6-depended manner (FIG. 9). Precipitation of gp130-$C_H1$●IL-6Rα-κ by Protein A-Sepharose was determined by western blotting with an anti-kappa specific HRP conjugate, which does not detect gp130-Fc●IL-6Rα-Fc. gp130-$C_H1$●IL-6Rα-κ could be precipitated by Protein A-Sepharose only when both gp130-Fc●IL-6Rα-Fc and IL-6 were present. This result conclusively indicates that IL-6 can induce ligand trap multimerization, and further indicate that the ligand trap can mimic the hexameric cytokine●Rα●signal transducer complex (FIG. 1). Ligand-induced multimerization may play a significant role in the clearance of cytokine●ligand trap complexes in vivo.

The biological activity of the different ligand traps may be further tested in assays which measure ligand-depended cell proliferation. Several cell proliferation assays exist for IL-6 and they employ cell lines such as B9, CESS, or XG-1. An example of this type of assay using the XG-1 cell line is presented below: XG-1 is a cell line derived from a human multiple myeloma (Zhang, et al., Blood 83:3654–3663

Figure 20:
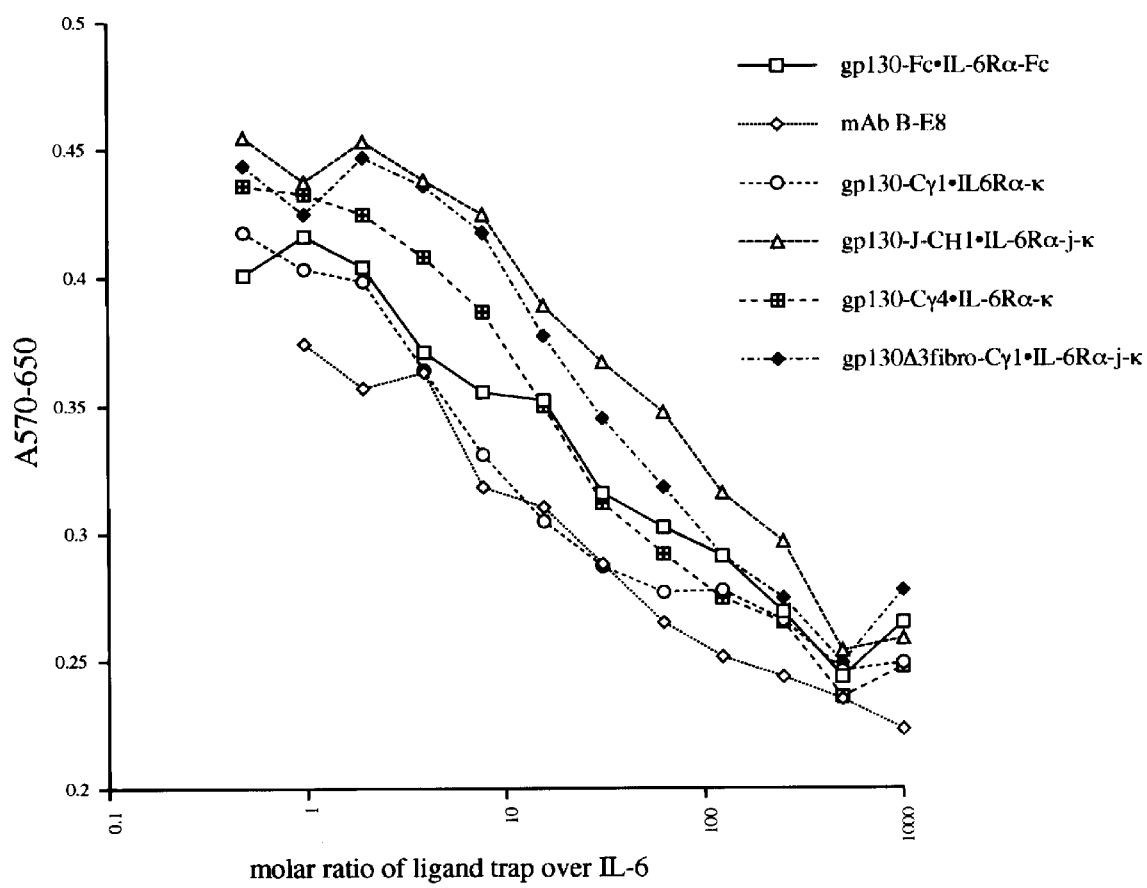
FIG. 20. Inhibition of IL-6-dependent XG-1 cell proliferation. XG-1 cells [Zhang, et al., Blood 83:3654–3663 (1994)] were prepared for a proliferation assay by starving the cells from IL-6 for 5 hours. Assays were set up in 96-well tissue culture dishes in RPMI+10% fetal calf serum+penicillin/streptomycin+0.050 nM 2-mercaptoethanol+glutamine. 0.1 ml of that media was used per well. Cells were suspended at a density of 250,000 per ml at the start of the assay. 72 hours post addition of IL-6±ligands traps or antibodies, an MTT assay was performed as described (Panayotatos et al. Biochemistry 33:5813–5818 (1994). The different ligand traps utilized are listed.

(1994). XG-1 depends on exogenously supplied human IL-6 for survival and proliferation. The $EC_{50}$ of IL-6 for the XG-1 line is approximately 50 pmoles/ml. The ability of several different IL-6 traps to block IL-6-depended proliferation of XG-1 cells was tested by incubating increasing amounts of purified ligand traps with 50 pg/ml IL-6 in XG-1 cultures. The ligand traps which were tested had been expressed and purified by methods similar to those described above. All of the ligand traps tested were found to inhibit IL-6-dependent proliferation of XG-1 in a dose dependent manner (FIG. 20). Of the five different traps tested gp130-Cγ1●IL-6Rα-κ was the most active and essentially display the same neutralizing activity towards IL-6 as the antibody B-E8. As little as a 10-fold molar excess of either gp130-Cγ1●IL-6Rα-κ or B-E8 completely blocked the activity of IL-6 (a reading of A570–650=0.3 AU corresponds to no proliferation of the XG-1 cells). At a 100-fold molar excess all of the ligand traps tested completely blocked the activity of IL-6. This observed inhibition is highly selective as neither a gp130-Fc●CNTFRα-Fc ligand trap which blocks CNTF activity, nor gp130-Fc homodimer exhibit any blocking activity towards IL-6 even when used at a 1000-fold molar excess over IL-6 (data not shown). This data demonstrates that the heteromeric immunoglobulin heavy/light chain receptor-based ligand traps function as selective high affinity antagonists of their cognate ligand.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

His His His His His His
1               5

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

Cys Gly Thr Glu Gly Gln Val Glu Arg Phe Glu Thr Val Gly Met Glu
1               5                   10                  15

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:3:

CGCCGCCACC ATGGTG                                                                           16

( 2 ) INFORMATION FOR SEQ ID NO:4:

( i ) SEQUENCE CHARACTERISTICS:
        ( A ) LENGTH: 10 amino acids
        ( B ) TYPE: amino acid (D) TOPOLOGY: unknown (ii) MOLECULE TYPE: peptide (xi) SEQUENCE DESCRIPTION: SEQ ID NO:4:

| Gly | Gln | Gly | Thr | Leu | Val | Thr | Val | Ser | Ser |
|---|---|---|---|---|---|---|---|---|---|
| 1 | | | | 5 | | | | | 10 |

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (xi) SEQUENCE DESCRIPTION: SEQ ID NO:5:

| Thr | Phe | Gly | Gln | Gly | Thr | Lys | Val | Glu | Ile | Lys |
|---|---|---|---|---|---|---|---|---|---|---|
| 1 | | | | 5 | | | | | 10 | |

(2) INFORMATION FOR SEQ ID NO:6:

(i) SEQUENCE CHARACTERISTICS:
        (A) LENGTH: 859 amino acids
        (B) TYPE: amino acid
        (D) TOPOLOGY: unknown (ii) MOLECULE TYPE: protein (xi) SEQUENCE DESCRIPTION: SEQ ID NO:6:

| Met | Val | Thr | Leu | Gln | Thr | Trp | Val | Val | Gln | Ala | Leu | Phe | Ile | Phe | Leu |
|---|---|---|---|---|---|---|---|---|---|---|---|---|---|---|---|
| 1 | | | | 5 | | | | | 10 | | | | | 15 | |
| Thr | Thr | Glu | Ser | Thr | Gly | Glu | Leu | Leu | Asp | Pro | Cys | Gly | Tyr | Ile | Ser |
| | | | 20 | | | | | 25 | | | | | 30 | | |
| Pro | Glu | Ser | Pro | Val | Val | Gln | Leu | His | Ser | Asn | Phe | Thr | Ala | Val | Cys |
| | | 35 | | | | | 40 | | | | | 45 | | | |
| Val | Leu | Lys | Glu | Lys | Cys | Met | Asp | Tyr | Phe | His | Val | Asn | Ala | Asn | Tyr |
| | 50 | | | | | 55 | | | | | 60 | | | | |
| Ile | Val | Trp | Lys | Thr | Asn | His | Phe | Thr | Ile | Pro | Lys | Glu | Gln | Tyr | Thr |
| 65 | | | | | 70 | | | | | 75 | | | | | 80 |
| Ile | Ile | Asn | Arg | Thr | Ala | Ser | Ser | Val | Thr | Phe | Thr | Asp | Ile | Ala | Ser |
| | | | | 85 | | | | | 90 | | | | | 95 | |
| Leu | Asn | Ile | Gln | Leu | Thr | Cys | Asn | Ile | Leu | Thr | Phe | Gly | Gln | Leu | Glu |
| | | | | 100 | | | | | 105 | | | | | 110 | |
| Gln | Asn | Val | Tyr | Gly | Ile | Thr | Ile | Ile | Ser | Gly | Leu | Pro | Pro | Glu | Lys |
| | | | 115 | | | | | 120 | | | | | 125 | | |
| Pro | Lys | Asn | Leu | Ser | Cys | Ile | Val | Asn | Glu | Gly | Lys | Lys | Met | Arg | Cys |
| | | 130 | | | | | 135 | | | | | 140 | | | |
| Glu | Trp | Asp | Gly | Gly | Arg | Glu | Thr | His | Leu | Glu | Thr | Asn | Phe | Thr | Leu |
| 145 | | | | | 150 | | | | | 155 | | | | | 160 |
| Lys | Ser | Glu | Trp | Ala | Thr | His | Lys | Phe | Ala | Asp | Cys | Lys | Ala | Lys | Arg |
| | | | | 165 | | | | | 170 | | | | | 175 | |
| Asp | Thr | Pro | Thr | Ser | Cys | Thr | Val | Asp | Tyr | Ser | Thr | Val | Tyr | Phe | Val |
| | | | | 180 | | | | | 185 | | | | | 190 | |
| Asn | Ile | Glu | Val | Trp | Val | Glu | Ala | Glu | Asn | Ala | Leu | Gly | Lys | Val | Thr |
| | | | 195 | | | | | 200 | | | | | 205 | | |
| Ser | Asp | His | Ile | Asn | Phe | Asp | Pro | Val | Tyr | Lys | Val | Lys | Pro | Asn | Pro |
| | | 210 | | | | | 215 | | | | | 220 | | | |
| Pro | His | Asn | Leu | Ser | Val | Ile | Asn | Ser | Glu | Glu | Leu | Ser | Ser | Ile | Leu |
| 225 | | | | | 230 | | | | | 235 | | | | | 240 |

```
Lys  Leu  Thr  Trp  Thr  Asn  Pro  Ser  Ile  Lys  Ser  Val  Ile  Ile  Leu  Lys
               245                     250                          255

Tyr  Asn  Ile  Gln  Tyr  Arg  Thr  Lys  Asp  Ala  Ser  Thr  Trp  Ser  Gln  Ile
               260                     265                     270

Pro  Pro  Glu  Asp  Thr  Ala  Ser  Thr  Arg  Ser  Ser  Phe  Thr  Val  Gln  Asp
               275                     280                     285

Leu  Lys  Pro  Phe  Thr  Glu  Tyr  Val  Phe  Arg  Ile  Arg  Cys  Met  Lys  Glu
          290                     295                     300

Asp  Gly  Lys  Gly  Tyr  Trp  Ser  Asp  Trp  Ser  Glu  Glu  Ala  Ser  Gly  Ile
305                           310                     315                      320

Thr  Tyr  Glu  Asp  Arg  Pro  Ser  Lys  Ala  Pro  Ser  Phe  Trp  Tyr  Lys  Ile
                    325                     330                          335

Asp  Pro  Ser  His  Thr  Gln  Gly  Tyr  Arg  Thr  Val  Gln  Leu  Val  Trp  Lys
               340                     345                          350

Thr  Leu  Pro  Pro  Phe  Glu  Ala  Asn  Gly  Lys  Ile  Leu  Asp  Tyr  Glu  Val
          355                     360                     365

Thr  Leu  Thr  Arg  Trp  Lys  Ser  His  Leu  Gln  Asn  Tyr  Thr  Val  Asn  Ala
370                           375                     380

Thr  Lys  Leu  Thr  Val  Asn  Leu  Thr  Asn  Asp  Arg  Tyr  Leu  Ala  Thr  Leu
385                      390                     395                           400

Thr  Val  Arg  Asn  Leu  Val  Gly  Lys  Ser  Asp  Ala  Ala  Val  Leu  Thr  Ile
               405                     410                          415

Pro  Ala  Cys  Asp  Phe  Gln  Ala  Thr  His  Pro  Val  Met  Asp  Leu  Lys  Ala
               420                     425                     430

Phe  Pro  Lys  Asp  Asn  Met  Leu  Trp  Val  Glu  Trp  Thr  Thr  Pro  Arg  Glu
          435                     440                     445

Ser  Val  Lys  Lys  Tyr  Ile  Leu  Glu  Trp  Cys  Val  Leu  Ser  Asp  Lys  Ala
     450                     455                     460

Pro  Cys  Ile  Thr  Asp  Trp  Gln  Gln  Glu  Asp  Gly  Thr  Val  His  Arg  Thr
465                           470                     475                      480

Tyr  Leu  Arg  Gly  Asn  Leu  Ala  Glu  Ser  Lys  Cys  Tyr  Leu  Ile  Thr  Val
                    485                     490                          495

Thr  Pro  Val  Tyr  Ala  Asp  Gly  Pro  Gly  Ser  Pro  Glu  Ser  Ile  Lys  Ala
               500                     505                     510

Tyr  Leu  Lys  Gln  Ala  Pro  Pro  Ser  Lys  Gly  Pro  Thr  Val  Arg  Thr  Lys
          515                     520                     525

Lys  Val  Gly  Lys  Asn  Glu  Ala  Val  Leu  Glu  Trp  Asp  Gln  Leu  Pro  Val
     530                     535                     540

Asp  Val  Gln  Asn  Gly  Phe  Ile  Arg  Asn  Tyr  Thr  Ile  Phe  Tyr  Arg  Thr
545                      550                     555                           560

Ile  Ile  Gly  Asn  Glu  Thr  Ala  Val  Asn  Val  Asp  Ser  Ser  His  Thr  Glu
               565                     570                          575

Tyr  Thr  Leu  Ser  Ser  Leu  Thr  Ser  Asp  Thr  Leu  Tyr  Met  Val  Arg  Met
               580                     585                     590

Ala  Ala  Tyr  Thr  Asp  Glu  Gly  Gly  Lys  Asp  Gly  Pro  Glu  Phe  Thr  Phe
          595                     600                     605

Thr  Thr  Pro  Lys  Phe  Ala  Gln  Gly  Glu  Ile  Glu  Ser  Gly  Glu  Pro  Lys
     610                     615                     620

Ser  Cys  Asp  Lys  Thr  His  Thr  Cys  Pro  Pro  Cys  Pro  Ala  Pro  Glu  Leu
625                      630                     635                           640

Leu  Gly  Gly  Pro  Ser  Val  Phe  Leu  Phe  Pro  Pro  Lys  Pro  Lys  Asp  Thr
               645                     650                          655

Leu  Met  Ile  Ser  Arg  Thr  Pro  Glu  Val  Thr  Cys  Val  Val  Val  Asp  Val
```

-continued

|     |     |     |     |     | 660 |     |     |     |     | 665 |     |     |     |     | 670 |
|-----|-----|-----|-----|-----|-----|-----|-----|-----|-----|-----|-----|-----|-----|-----|-----|
| Ser | His | Glu | Asp | Pro | Glu | Val | Lys | Phe | Asn | Trp | Tyr | Val | Asp | Gly | Val |
|     | 675 |     |     |     | 680 |     |     |     |     | 685 |     |     |     |     |     |
| Glu | Val | His | Asn | Ala | Lys | Thr | Lys | Pro | Arg | Glu | Glu | Gln | Tyr | Asn | Ser |
| 690 |     |     |     |     | 695 |     |     |     |     | 700 |     |     |     |     |     |
| Thr | Tyr | Arg | Val | Val | Ser | Val | Leu | Thr | Val | Leu | His | Gln | Asp | Trp | Leu |
| 705 |     |     |     |     | 710 |     |     |     |     | 715 |     |     |     |     | 720 |
| Asn | Gly | Lys | Glu | Tyr | Lys | Cys | Lys | Val | Ser | Asn | Lys | Ala | Leu | Pro | Ala |
|     |     |     |     | 725 |     |     |     |     | 730 |     |     |     |     | 735 |     |
| Pro | Ile | Glu | Lys | Thr | Ile | Ser | Lys | Ala | Lys | Gly | Gln | Pro | Arg | Glu | Pro |
|     |     |     | 740 |     |     |     |     | 745 |     |     |     |     | 750 |     |     |
| Gln | Val | Tyr | Thr | Leu | Pro | Pro | Ser | Arg | Asp | Glu | Leu | Thr | Lys | Asn | Gln |
|     |     | 755 |     |     |     |     | 760 |     |     |     |     | 765 |     |     |     |
| Val | Ser | Leu | Thr | Cys | Leu | Val | Lys | Gly | Phe | Tyr | Pro | Ser | Asp | Ile | Ala |
|     | 770 |     |     |     |     | 775 |     |     |     |     | 780 |     |     |     |     |
| Val | Glu | Trp | Glu | Ser | Asn | Gly | Gln | Pro | Glu | Asn | Asn | Tyr | Lys | Thr | Thr |
| 785 |     |     |     |     | 790 |     |     |     |     | 795 |     |     |     |     | 800 |
| Pro | Pro | Val | Leu | Asp | Ser | Asp | Gly | Ser | Phe | Phe | Leu | Tyr | Ser | Lys | Leu |
|     |     |     |     | 805 |     |     |     |     | 810 |     |     |     |     | 815 |     |
| Thr | Val | Asp | Lys | Ser | Arg | Trp | Gln | Gln | Gly | Asn | Val | Phe | Ser | Cys | Ser |
|     |     |     | 820 |     |     |     |     | 825 |     |     |     |     | 830 |     |     |
| Val | Met | His | Glu | Ala | Leu | His | Asn | His | Tyr | Thr | Gln | Lys | Ser | Leu | Ser |
|     |     | 835 |     |     |     |     | 840 |     |     |     |     | 845 |     |     |     |
| Leu | Ser | Pro | Gly | Lys | His | His | His | His | His |     |     |     |     |     |     |
|     | 850 |     |     |     |     | 855 |     |     |     |     |     |     |     |     |     |

( 2 ) INFORMATION FOR SEQ ID NO:7:

( i ) SEQUENCE CHARACTERISTICS:
        ( A ) LENGTH: 592 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:7:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Val | Ala | Val | Gly | Cys | Ala | Leu | Leu | Ala | Ala | Leu | Leu | Ala | Ala | Pro |
| 1   |     |     |     | 5   |     |     |     |     | 10  |     |     |     |     | 15  |     |
| Gly | Ala | Ala | Leu | Ala | Pro | Arg | Arg | Cys | Pro | Ala | Gln | Glu | Val | Ala | Arg |
|     |     |     | 20  |     |     |     |     | 25  |     |     |     |     | 30  |     |     |
| Gly | Val | Leu | Thr | Ser | Leu | Pro | Gly | Asp | Ser | Val | Thr | Leu | Thr | Cys | Pro |
|     |     |     | 35  |     |     |     |     | 40  |     |     |     |     | 45  |     |     |
| Gly | Val | Glu | Pro | Glu | Asp | Asn | Ala | Thr | Val | His | Trp | Val | Leu | Arg | Lys |
|     | 50  |     |     |     |     | 55  |     |     |     |     | 60  |     |     |     |     |
| Pro | Ala | Ala | Gly | Ser | His | Pro | Ser | Arg | Trp | Ala | Gly | Met | Gly | Arg | Arg |
| 65  |     |     |     |     | 70  |     |     |     |     | 75  |     |     |     |     | 80  |
| Leu | Leu | Leu | Arg | Ser | Val | Gln | Leu | His | Asp | Ser | Gly | Asn | Tyr | Ser | Cys |
|     |     |     |     | 85  |     |     |     |     | 90  |     |     |     |     | 95  |     |
| Tyr | Arg | Ala | Gly | Arg | Pro | Ala | Gly | Thr | Val | His | Leu | Leu | Val | Asp | Val |
|     |     |     |     | 100 |     |     |     |     | 105 |     |     |     |     | 110 |     |
| Pro | Pro | Glu | Glu | Pro | Gln | Leu | Ser | Cys | Phe | Arg | Lys | Ser | Pro | Leu | Ser |
|     |     |     |     | 115 |     |     |     |     | 120 |     |     |     |     | 125 |     |
| Asn | Val | Val | Cys | Glu | Trp | Gly | Pro | Arg | Ser | Thr | Pro | Ser | Leu | Thr | Thr |
|     |     | 130 |     |     |     |     | 135 |     |     |     |     | 140 |     |     |     |
| Lys | Ala | Val | Leu | Leu | Val | Arg | Lys | Phe | Gln | Asn | Ser | Pro | Ala | Glu | Asp |
| 145 |     |     |     |     | 150 |     |     |     |     | 155 |     |     |     |     | 160 |

```
Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ala Gly Glu Pro Lys Ser Cys Asp Lys Thr
            355                 360                 365

His Thr Cys Pro Pro Cys Pro Ala Pro Glu Leu Leu Gly Gly Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
    450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
            485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590
```

( 2 ) INFORMATION FOR SEQ ID NO:8:

( i ) SEQUENCE CHARACTERISTICS:
        ( A ) LENGTH: 951 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

```
Met Val Thr Leu Gln Thr Trp Val Val Gln Ala Leu Phe Ile Phe Leu
  1               5                  10                  15

Thr Thr Glu Ser Thr Gly Glu Leu Leu Asp Pro Cys Gly Tyr Ile Ser
             20                  25                  30

Pro Glu Ser Pro Val Val Gln Leu His Ser Asn Phe Thr Ala Val Cys
             35                  40                  45

Val Leu Lys Glu Lys Cys Met Asp Tyr Phe His Val Asn Ala Asn Tyr
         50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
                100                 105                 110

Gln Asn Val Tyr Gly Ile Thr Ile Ile Ser Gly Leu Pro Pro Glu Lys
            115                 120                 125

Pro Lys Asn Leu Ser Cys Ile Val Asn Glu Gly Lys Lys Met Arg Cys
        130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
            195                 200                 205

Ser Asp His Ile Asn Phe Asp Pro Val Tyr Lys Val Lys Pro Asn Pro
        210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
        290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
```

-continued

```
                          355                        360                          365
    Thr  Leu  Thr  Arg  Trp  Lys  Ser  His  Leu  Gln  Asn  Tyr  Thr  Val  Asn  Ala
              370                      375                        380
    Thr  Lys  Leu  Thr  Val  Asn  Leu  Thr  Asn  Asp  Arg  Tyr  Leu  Ala  Thr  Leu
    385                      390                        395                       400
    Thr  Val  Arg  Asn  Leu  Val  Gly  Lys  Ser  Asp  Ala  Ala  Val  Leu  Thr  Ile
                             405                       410                       415
    Pro  Ala  Cys  Asp  Phe  Gln  Ala  Thr  His  Pro  Val  Met  Asp  Leu  Lys  Ala
                   420                      425                        430
    Phe  Pro  Lys  Asp  Asn  Met  Leu  Trp  Val  Glu  Trp  Thr  Thr  Pro  Arg  Glu
                   435                      440                        445
    Ser  Val  Lys  Lys  Tyr  Ile  Leu  Glu  Trp  Cys  Val  Leu  Ser  Asp  Lys  Ala
              450                      455                        460
    Pro  Cys  Ile  Thr  Asp  Trp  Gln  Gln  Glu  Asp  Gly  Thr  Val  His  Arg  Thr
    465                      470                        475                       480
    Tyr  Leu  Arg  Gly  Asn  Leu  Ala  Glu  Ser  Lys  Cys  Tyr  Leu  Ile  Thr  Val
                             485                       490                       495
    Thr  Pro  Val  Tyr  Ala  Asp  Gly  Pro  Gly  Ser  Pro  Glu  Ser  Ile  Lys  Ala
                   500                      505                        510
    Tyr  Leu  Lys  Gln  Ala  Pro  Pro  Ser  Lys  Gly  Pro  Thr  Val  Arg  Thr  Lys
                   515                      520                        525
    Lys  Val  Gly  Lys  Asn  Glu  Ala  Val  Leu  Glu  Trp  Asp  Gln  Leu  Pro  Val
              530                      535                        540
    Asp  Val  Gln  Asn  Gly  Phe  Ile  Arg  Asn  Tyr  Thr  Ile  Phe  Tyr  Arg  Thr
    545                      550                        555                       560
    Ile  Ile  Gly  Asn  Glu  Thr  Ala  Val  Asn  Val  Asp  Ser  Ser  His  Thr  Glu
                             565                       570                       575
    Tyr  Thr  Leu  Ser  Ser  Leu  Thr  Ser  Asp  Thr  Leu  Tyr  Met  Val  Arg  Met
                   580                      585                        590
    Ala  Ala  Tyr  Thr  Asp  Glu  Gly  Gly  Lys  Asp  Gly  Pro  Glu  Phe  Thr  Phe
                   595                      600                        605
    Thr  Thr  Pro  Lys  Phe  Ala  Gln  Gly  Glu  Ile  Glu  Ser  Gly  Ala  Ser  Thr
              610                      615                        620
    Lys  Gly  Pro  Ser  Val  Phe  Pro  Leu  Ala  Pro  Ser  Ser  Lys  Ser  Thr  Ser
    625                      630                        635                       640
    Gly  Gly  Thr  Ala  Ala  Leu  Gly  Cys  Leu  Val  Lys  Asp  Tyr  Phe  Pro  Glu
                             645                       650                       655
    Pro  Val  Thr  Val  Ser  Trp  Asn  Ser  Gly  Ala  Leu  Thr  Ser  Gly  Val  His
                   660                      665                        670
    Thr  Phe  Pro  Ala  Val  Leu  Gln  Ser  Ser  Gly  Leu  Tyr  Ser  Leu  Ser  Ser
                   675                      680                        685
    Val  Val  Thr  Val  Pro  Ser  Ser  Ser  Leu  Gly  Thr  Gln  Thr  Tyr  Ile  Cys
              690                      695                        700
    Asn  Val  Asn  His  Lys  Pro  Ser  Asn  Thr  Lys  Val  Asp  Lys  Lys  Val  Glu
    705                      710                        715                       720
    Pro  Lys  Ser  Cys  Asp  Lys  Thr  His  Thr  Cys  Pro  Pro  Cys  Pro  Ala  Pro
                   725                      730                        735
    Glu  Leu  Leu  Gly  Gly  Pro  Ser  Val  Phe  Leu  Phe  Pro  Pro  Lys  Pro  Lys
                   740                      745                        750
    Asp  Thr  Leu  Met  Ile  Ser  Arg  Thr  Pro  Glu  Val  Thr  Cys  Val  Val  Val
              755                      760                        765
    Asp  Val  Ser  His  Glu  Asp  Pro  Glu  Val  Lys  Phe  Asn  Trp  Tyr  Val  Asp
    770                      775                        780
```

| | | | | | | | | | | | | | | |
|---|---|---|---|---|---|---|---|---|---|---|---|---|---|---|
|Gly<br>785|Val|Glu|Val|His|Asn<br>790|Ala|Lys|Thr|Lys|Pro<br>795|Arg|Glu|Glu|Gln|Tyr<br>800|
|Asn|Ser|Thr|Tyr|Arg<br>805|Val|Val|Ser|Val|Leu<br>810|Thr|Val|Leu|His|Gln|Asp<br>815|
|Trp|Leu|Asn|Gly<br>820|Lys|Glu|Tyr|Lys|Cys<br>825|Lys|Val|Ser|Asn|Lys<br>830|Ala|Leu|
|Pro|Ala|Pro<br>835|Ile|Glu|Lys|Thr|Ile<br>840|Ser|Lys|Ala|Lys|Gly<br>845|Gln|Pro|Arg|
|Glu|Pro<br>850|Gln|Val|Tyr|Thr|Leu<br>855|Pro|Pro|Ser|Arg|Asp<br>860|Glu|Leu|Thr|Lys|
|Asn<br>865|Gln|Val|Ser|Leu|Thr<br>870|Cys|Leu|Val|Lys|Gly<br>875|Phe|Tyr|Pro|Ser|Asp<br>880|
|Ile|Ala|Val|Glu|Trp<br>885|Glu|Ser|Asn|Gly|Gln<br>890|Pro|Glu|Asn|Asn|Tyr|Lys<br>895|
|Thr|Thr|Pro|Pro<br>900|Val|Leu|Asp|Ser|Asp<br>905|Gly|Ser|Phe|Phe|Leu<br>910|Tyr|Ser|
|Lys|Leu|Thr<br>915|Val|Asp|Lys|Ser|Arg|Trp<br>920|Gln|Gln|Gly|Asn<br>925|Val|Phe|Ser|
|Cys|Ser<br>930|Val|Met|His|Glu|Ala<br>935|Leu|His|Asn|His|Tyr<br>940|Thr|Gln|Lys|Ser|
|Leu|Ser<br>945|Leu|Ser|Pro|Gly<br>950|Lys| | | | | | | | | |

( 2 ) INFORMATION FOR SEQ ID NO:9:

( i ) SEQUENCE CHARACTERISTICS:
        ( A ) LENGTH: 332 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

| | | | | | | | | | | | | | | |
|---|---|---|---|---|---|---|---|---|---|---|---|---|---|---|
|Met<br>1|Val|Thr|Leu|Gln<br>5|Thr|Trp|Val|Val|Gln<br>10|Ala|Leu|Phe|Ile|Phe|Leu<br>15|
|Thr|Thr|Glu|Ser<br>20|Thr|Gly|Glu|Leu|Leu<br>25|Asp|Pro|Cys|Gly|Tyr<br>30|Ile|Ser|
|Pro|Glu|Ser<br>35|Pro|Val|Val|Gln|Leu<br>40|His|Ser|Asn|Phe|Thr<br>45|Ala|Val|Cys|
|Val|Leu<br>50|Lys|Glu|Lys|Cys|Met<br>55|Asp|Tyr|Phe|His|Val<br>60|Asn|Ala|Asn|Tyr|
|Ile<br>65|Val|Trp|Lys|Thr|Asn<br>70|His|Phe|Thr|Ile|Pro<br>75|Lys|Glu|Gln|Tyr|Thr<br>80|
|Ile|Ile|Asn|Arg|Thr<br>85|Ala|Ser|Ser|Val|Thr<br>90|Phe|Thr|Asp|Ile|Ala<br>95|Ser|
|Leu|Asn|Ile|Gln|Leu<br>100|Thr|Cys|Asn|Ile|Leu<br>105|Thr|Phe|Gly|Gln|Leu<br>110|Glu|
|Gln|Asn|Val|Tyr<br>115|Gly|Ile|Thr|Ile|Ile<br>120|Ser|Gly|Leu|Pro|Pro<br>125|Glu|Lys|
|Pro|Lys|Asn<br>130|Leu|Ser|Cys|Ile|Val<br>135|Asn|Glu|Gly|Lys|Lys<br>140|Met|Arg|Cys|
|Glu|Trp<br>145|Asp|Gly|Gly|Arg|Glu<br>150|Thr|His|Leu|Glu|Thr<br>155|Asn|Phe|Thr|Leu<br>160|
|Lys|Ser|Glu|Trp|Ala<br>165|Thr|His|Lys|Phe|Ala<br>170|Asp|Cys|Lys|Ala|Lys<br>175|Arg|
|Asp|Thr|Pro|Thr<br>180|Ser|Cys|Thr|Val|Asp<br>185|Tyr|Ser|Thr|Val|Tyr<br>190|Phe|Val|

```
Asn  Ile  Glu  Val  Trp  Val  Glu  Ala  Glu  Asn  Ala  Leu  Gly  Lys  Val  Thr
          195                 200                      205

Ser  Asp  His  Ile  Asn  Phe  Asp  Pro  Val  Tyr  Lys  Val  Lys  Pro  Asn  Pro
     210                      215                      220

Pro  His  Asn  Leu  Ser  Val  Ile  Asn  Ser  Glu  Glu  Leu  Ser  Ser  Ile  Leu
225                      230                 235                           240

Lys  Leu  Thr  Trp  Thr  Asn  Pro  Ser  Ile  Lys  Ser  Val  Ile  Ile  Leu  Lys
               245                           250                      255

Tyr  Asn  Ile  Gln  Tyr  Arg  Thr  Lys  Asp  Ala  Ser  Thr  Trp  Ser  Gln  Ile
          260                      265                      270

Pro  Pro  Glu  Asp  Thr  Ala  Ser  Thr  Arg  Ser  Ser  Phe  Thr  Val  Gln  Asp
          275                 280                      285

Leu  Lys  Pro  Phe  Thr  Glu  Tyr  Val  Phe  Arg  Ile  Arg  Cys  Met  Lys  Glu
     290                      295                      300

Asp  Gly  Lys  Gly  Tyr  Trp  Ser  Asp  Trp  Ser  Glu  Glu  Ala  Ser  Gly  Ile
305                      310                 315                           320

Thr  Tyr  Glu  Asp  Arg  Pro  Ser  Lys  Ala  Pro  Ser  Gly
               325                      330
```

( 2 ) INFORMATION FOR SEQ ID NO:10:

( i ) SEQUENCE CHARACTERISTICS:
        ( A ) LENGTH: 120 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

```
Ser  Gly  Gly  Gln  Gly  Thr  Leu  Val  Thr  Val  Ser  Ser  Ala  Ser  Thr  Lys
1              5                   10                      15

Gly  Pro  Ser  Val  Phe  Pro  Leu  Ala  Pro  Ser  Ser  Lys  Ser  Thr  Ser  Gly
               20                      25                      30

Gly  Thr  Ala  Ala  Leu  Gly  Cys  Leu  Val  Lys  Asp  Tyr  Phe  Pro  Glu  Pro
          35                      40                      45

Val  Thr  Val  Ser  Trp  Asn  Ser  Gly  Ala  Leu  Thr  Ser  Gly  Val  His  Thr
     50                      55                      60

Phe  Pro  Ala  Val  Leu  Gln  Ser  Ser  Gly  Leu  Tyr  Ser  Leu  Ser  Ser  Val
65                      70                      75                           80

Val  Thr  Val  Pro  Ser  Ser  Ser  Leu  Gly  Thr  Gln  Thr  Tyr  Ile  Cys  Asn
               85                      90                      95

Val  Asn  His  Lys  Pro  Ser  Asn  Thr  Lys  Val  Asp  Lys  Lys  Val  Glu  Pro
               100                     105                     110

Lys  Ser  Cys  Asp  Lys  Thr  His  Thr
          115                 120
```

( 2 ) INFORMATION FOR SEQ ID NO:11:

( i ) SEQUENCE CHARACTERISTICS:
        ( A ) LENGTH: 329 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

```
Ser  Gly  Ala  Ser  Thr  Lys  Gly  Pro  Ser  Val  Phe  Pro  Leu  Ala  Pro  Cys
1              5                   10                      15

Ser  Arg  Ser  Thr  Ser  Glu  Ser  Thr  Ala  Ala  Leu  Gly  Cys  Leu  Val  Lys
```

```
                          20                     25                      30
     Asp  Tyr  Phe  Pro  Glu  Pro  Val  Thr  Val  Ser  Trp  Asn  Ser  Gly  Ala  Leu
               35                      40                     45

Thr  Ser  Gly  Val  His  Thr  Phe  Pro  Ala  Val  Leu  Gln  Ser  Ser  Gly  Leu
          50                      55                     60

Tyr  Ser  Leu  Ser  Ser  Val  Val  Thr  Val  Pro  Ser  Ser  Ser  Leu  Gly  Thr
     65                      70                     75                          80

Lys  Thr  Tyr  Thr  Cys  Asn  Val  Asp  His  Lys  Pro  Ser  Asn  Thr  Lys  Val
                    85                     90                          95

Asp  Lys  Arg  Val  Glu  Ser  Lys  Tyr  Gly  Pro  Pro  Cys  Pro  Ser  Cys  Pro
                    100                    105                    110

Ala  Pro  Glu  Phe  Leu  Gly  Gly  Pro  Ser  Val  Phe  Leu  Phe  Pro  Pro  Lys
                    115                    120                    125

Pro  Lys  Asp  Thr  Leu  Met  Ile  Ser  Arg  Thr  Pro  Glu  Val  Thr  Cys  Val
          130                    135                    140

Val  Val  Asp  Val  Ser  Gln  Glu  Asp  Pro  Glu  Val  Gln  Phe  Asn  Trp  Tyr
     145                    150                    155                         160

Val  Asp  Gly  Val  Glu  Val  His  Asn  Ala  Lys  Thr  Lys  Pro  Arg  Glu  Glu
                         165                    170                    175

Gln  Phe  Asn  Ser  Thr  Tyr  Arg  Val  Val  Ser  Val  Leu  Thr  Val  Leu  His
                    180                    185                    190

Gln  Asp  Trp  Leu  Asn  Gly  Lys  Glu  Tyr  Lys  Cys  Lys  Val  Ser  Asn  Lys
               195                    200                    205

Gly  Leu  Pro  Ser  Ser  Ile  Glu  Lys  Thr  Ile  Ser  Lys  Ala  Lys  Gly  Gln
          210                    215                    220

Pro  Arg  Glu  Pro  Gln  Val  Tyr  Thr  Leu  Pro  Pro  Ser  Gln  Glu  Glu  Met
     225                    230                    235                         240

Thr  Lys  Asn  Gln  Val  Ser  Leu  Thr  Cys  Leu  Val  Lys  Gly  Phe  Tyr  Pro
                    245                    250                    255

Ser  Asp  Ile  Ala  Val  Glu  Trp  Glu  Ser  Asn  Gly  Gln  Pro  Glu  Asn  Asn
                    260                    265                    270

Tyr  Lys  Thr  Thr  Pro  Pro  Val  Leu  Asp  Ser  Asp  Gly  Ser  Phe  Phe  Leu
               275                    280                    285

Tyr  Ser  Arg  Leu  Thr  Val  Asp  Lys  Ser  Arg  Trp  Gln  Glu  Gly  Asn  Val
          290                    295                    300

Phe  Ser  Cys  Ser  Val  Met  His  Glu  Ala  Leu  His  Asn  His  Tyr  Thr  Gln
     305                    310                    315                         320

Lys  Ser  Leu  Ser  Leu  Ser  Leu  Gly  Lys
                    325
```

( 2 ) INFORMATION FOR SEQ ID NO:12:

( i ) SEQUENCE CHARACTERISTICS:
        ( A ) LENGTH: 108 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:12:

```
     Ser  Gly  Thr  Val  Ala  Ala  Pro  Ser  Val  Phe  Ile  Phe  Pro  Pro  Ser  Asp
     1                   5                      10                         15

Glu  Gln  Leu  Lys  Ser  Gly  Thr  Ala  Ser  Val  Val  Cys  Leu  Leu  Asn  Asn
                    20                     25                     30

Phe  Tyr  Pro  Arg  Glu  Ala  Lys  Val  Gln  Trp  Lys  Val  Asp  Asn  Ala  Leu
               35                      40                     45
```

```
        Gln  Ser  Gly  Asn  Ser  Gln  Glu  Ser  Val  Thr  Glu  Gln  Asp  Ser  Lys  Asp
             50                       55                       60

Ser  Thr  Tyr  Ser  Leu  Ser  Ser  Thr  Leu  Thr  Leu  Ser  Lys  Ala  Asp  Tyr
        65                       70                       75                       80

Glu  Lys  His  Lys  Val  Tyr  Ala  Cys  Glu  Val  Thr  His  Gln  Gly  Leu  Ser
                            85                       90                       95

Ser  Pro  Val  Thr  Lys  Ser  Phe  Asn  Arg  Gly  Glu  Cys
                            100                      105
```

( 2 ) INFORMATION FOR SEQ ID NO:13:

( i ) SEQUENCE CHARACTERISTICS:
       ( A ) LENGTH: 106 amino acids
       ( B ) TYPE: amino acid
       ( D ) TOPOLOGY: unknown ( i i ) MOLECULE TYPE: peptide ( x i ) SEQUENCE DESCRIPTION: SEQ ID NO:13:

```
        Ser  Gly  Pro  Lys  Ala  Ala  Pro  Ser  Val  Thr  Leu  Phe  Pro  Pro  Ser  Ser
        1                   5                        10                       15

Glu  Glu  Leu  Gln  Ala  Asn  Lys  Ala  Thr  Leu  Val  Cys  Leu  Ile  Ser  Asp
                            20                       25                       30

Phe  Tyr  Pro  Gly  Ala  Val  Thr  Val  Ala  Trp  Lys  Ala  Asp  Ser  Ser  Pro
                            35                       40                       45

Val  Lys  Ala  Gly  Val  Glu  Thr  Thr  Thr  Pro  Ser  Lys  Gln  Ser  Asn  Asn
             50                       55                       60

Lys  Tyr  Ala  Ala  Ser  Ser  Tyr  Leu  Ser  Leu  Thr  Pro  Glu  Gln  Trp  Lys
        65                       70                       75                       80

Ser  His  Arg  Ser  Tyr  Ser  Cys  Gln  Val  Thr  His  Glu  Gly  Ser  Thr  Val
                            85                       90                       95

Glu  Lys  Thr  Val  Ala  Pro  Thr  Glu  Cys  Ser
                            100                      105
```

( 2 ) INFORMATION FOR SEQ ID NO:14:

( i ) SEQUENCE CHARACTERISTICS:
       ( A ) LENGTH: 360 amino acids
       ( B ) TYPE: amino acid
       ( D ) TOPOLOGY: unknown ( i i ) MOLECULE TYPE: peptide ( x i ) SEQUENCE DESCRIPTION: SEQ ID NO:14:

```
        Met  Val  Ala  Val  Gly  Cys  Ala  Leu  Leu  Ala  Ala  Leu  Leu  Ala  Ala  Pro
        1                   5                        10                       15

Gly  Ala  Ala  Leu  Ala  Pro  Arg  Arg  Cys  Pro  Ala  Gln  Glu  Val  Ala  Arg
                            20                       25                       30

Gly  Val  Leu  Thr  Ser  Leu  Pro  Gly  Asp  Ser  Val  Thr  Leu  Thr  Cys  Pro
                            35                       40                       45

Gly  Val  Glu  Pro  Glu  Asp  Asn  Ala  Thr  Val  His  Trp  Val  Leu  Arg  Lys
             50                       55                       60

Pro  Ala  Ala  Gly  Ser  His  Pro  Ser  Arg  Trp  Ala  Gly  Met  Gly  Arg  Arg
        65                       70                       75                       80

Leu  Leu  Leu  Arg  Ser  Val  Gln  Leu  His  Asp  Ser  Gly  Asn  Tyr  Ser  Cys
                            85                       90                       95

Tyr  Arg  Ala  Gly  Arg  Pro  Ala  Gly  Thr  Val  His  Leu  Leu  Val  Asp  Val
                            100                      105                      110

Pro  Pro  Glu  Glu  Pro  Gln  Leu  Ser  Cys  Phe  Arg  Lys  Ser  Pro  Leu  Ser
                            115                      120                      125
```

```
Asn  Val  Val  Cys  Glu  Trp  Gly  Pro  Arg  Ser  Thr  Pro  Ser  Leu  Thr  Thr
     130                      135                 140

Lys  Ala  Val  Leu  Leu  Val  Arg  Lys  Phe  Gln  Asn  Ser  Pro  Ala  Glu  Asp
145                           150                 155                      160

Phe  Gln  Glu  Pro  Cys  Gln  Tyr  Ser  Gln  Glu  Ser  Gln  Lys  Phe  Ser  Cys
                    165                 170                           175

Gln  Leu  Ala  Val  Pro  Glu  Gly  Asp  Ser  Ser  Phe  Tyr  Ile  Val  Ser  Met
               180                      185                      190

Cys  Val  Ala  Ser  Ser  Val  Gly  Ser  Lys  Phe  Ser  Lys  Thr  Gln  Thr  Phe
          195                      200                      205

Gln  Gly  Cys  Gly  Ile  Leu  Gln  Pro  Asp  Pro  Ala  Asn  Ile  Thr  Val
     210                      215                      220

Thr  Ala  Val  Ala  Arg  Asn  Pro  Arg  Trp  Leu  Ser  Val  Thr  Trp  Gln  Asp
225                      230                      235                      240

Pro  His  Ser  Trp  Asn  Ser  Ser  Phe  Tyr  Arg  Leu  Arg  Phe  Glu  Leu  Arg
                    245                      250                      255

Tyr  Arg  Ala  Glu  Arg  Ser  Lys  Thr  Phe  Thr  Thr  Trp  Met  Val  Lys  Asp
               260                      265                      270

Leu  Gln  His  His  Cys  Val  Ile  His  Asp  Ala  Trp  Ser  Gly  Leu  Arg  His
          275                      280                      285

Val  Val  Gln  Leu  Arg  Ala  Gln  Glu  Glu  Phe  Gly  Gln  Gly  Glu  Trp  Ser
     290                      295                      300

Glu  Trp  Ser  Pro  Glu  Ala  Met  Gly  Thr  Pro  Trp  Thr  Glu  Ser  Arg  Ser
305                      310                      315                      320

Pro  Pro  Ala  Glu  Asn  Glu  Val  Ser  Thr  Pro  Met  Gln  Ala  Leu  Thr  Thr
                    325                      330                      335

Asn  Lys  Asp  Asp  Asp  Asn  Ile  Leu  Phe  Arg  Asp  Ser  Ala  Asn  Ala  Thr
               340                      345                      350

Ser  Leu  Pro  Val  Gln  Asp  Ala  Gly
          355                      360
```

(2) INFORMATION FOR SEQ ID NO:15:

(i) SEQUENCE CHARACTERISTICS:
        (A) LENGTH: 315 amino acids
        (B) TYPE: amino acid
        (D) TOPOLOGY: unknown (ii) MOLECULE TYPE: peptide (xi) SEQUENCE DESCRIPTION: SEQ ID NO:15:

```
Met  Val  Ala  Val  Gly  Cys  Ala  Leu  Leu  Ala  Ala  Leu  Leu  Ala  Ala  Pro
1                   5                   10                      15

Gly  Ala  Ala  Leu  Ala  Pro  Arg  Arg  Cys  Pro  Ala  Gln  Glu  Val  Ala  Arg
               20                  25                      30

Gly  Val  Leu  Thr  Ser  Leu  Pro  Gly  Asp  Ser  Val  Thr  Leu  Thr  Cys  Pro
          35                      40                      45

Gly  Val  Glu  Pro  Glu  Asp  Asn  Ala  Thr  Val  His  Trp  Val  Leu  Arg  Lys
     50                       55                      60

Pro  Ala  Ala  Gly  Ser  His  Pro  Ser  Arg  Trp  Ala  Gly  Met  Gly  Arg  Arg
65                       70                      75                       80

Leu  Leu  Leu  Arg  Ser  Val  Gln  Leu  His  Asp  Ser  Gly  Asn  Tyr  Ser  Cys
               85                      90                      95

Tyr  Arg  Ala  Gly  Arg  Pro  Ala  Gly  Thr  Val  His  Leu  Leu  Val  Asp  Val
               100                     105                     110

Pro  Pro  Glu  Glu  Pro  Gln  Leu  Ser  Cys  Phe  Arg  Lys  Ser  Pro  Leu  Ser
```

|  | 115 |  |  |  |  | 120 |  |  |  | 125 |  |  |  |
|---|---|---|---|---|---|---|---|---|---|---|---|---|---|
| Asn | Val<br>130 | Val | Cys | Glu | Trp | Gly<br>135 | Pro | Arg | Ser | Thr | Pro<br>140 | Ser | Leu | Thr | Thr |
| Lys<br>145 | Ala | Val | Leu | Leu | Val<br>150 | Arg | Lys | Phe | Gln | Asn<br>155 | Ser | Pro | Ala | Glu | Asp<br>160 |
| Phe | Gln | Glu | Pro | Cys<br>165 | Gln | Tyr | Ser | Gln | Glu<br>170 | Ser | Gln | Lys | Phe | Ser<br>175 | Cys |
| Gln | Leu | Ala | Val<br>180 | Pro | Glu | Gly | Asp | Ser<br>185 | Ser | Phe | Tyr | Ile | Val<br>190 | Ser | Met |
| Cys | Val | Ala<br>195 | Ser | Ser | Val | Gly<br>200 | Ser | Lys | Phe | Ser | Lys<br>205 | Thr | Gln | Thr | Phe |
| Gln | Gly<br>210 | Cys | Gly | Ile | Leu | Gln<br>215 | Pro | Asp | Pro | Pro | Ala<br>220 | Asn | Ile | Thr | Val |
| Thr<br>225 | Ala | Val | Ala | Arg | Asn<br>230 | Pro | Arg | Trp | Leu | Ser<br>235 | Val | Thr | Trp | Gln | Asp<br>240 |
| Pro | His | Ser | Trp | Asn<br>245 | Ser | Ser | Phe | Tyr | Arg<br>250 | Leu | Arg | Phe | Glu | Leu<br>255 | Arg |
| Tyr | Arg | Ala | Glu<br>260 | Arg | Ser | Lys | Thr | Phe<br>265 | Thr | Thr | Trp | Met | Val<br>270 | Lys | Asp |
| Leu | Gln | His<br>275 | His | Cys | Val | Ile | His<br>280 | Asp | Ala | Trp | Ser | Gly<br>285 | Leu | Arg | His |
| Val | Val<br>290 | Gln | Leu | Arg | Ala | Gln<br>295 | Glu | Glu | Phe | Gly | Gln<br>300 | Gly | Glu | Trp | Ser |
| Glu<br>305 | Trp | Ser | Pro | Glu | Ala<br>310 | Met | Gly | Thr | Thr | Gly<br>315 |  |  |  |  |  |

We claim:

1. A purified antagonist of a cytokine comprising:
a) the extracellular domain but not the transmembrane and cytoplasmic domains of the specificity determining component of the cytokine's receptor; and
b) the extracellular domain but not the transmembrane and cytoplasmic domains of a signal transducing component of the cytokine's receptor;
wherein the cytokine is selected from the group consisting of interleukin-1, interleukin-2, interleukin-3, interleukin-4, interleukin-5, interleukin-15, granulocyte macrophage colony stimulating factor, gamma-interferon, and Transforming Growth Factor-Beta, and the antagonist is capable of binding the cytokine to form a nonfunctional complex.

2. The purified antagonist according to claim 1, which further comprises an immunoglobulin derived domain capable of forming a complex between said extracellular domain of said specificity determining component and said extracellular domain of said signal transducing component.

3. The purified antagonist according to claim 2, in which said immunoglobulin domain is the Fc domain of IgG.

4. The purified antagonist according to claim 2, in which said immunoglobulin domain is a heavy chain of IgG.

5. The purified antagonist according to claim 4, in which said heavy chain is C-gamma1 or C-gamma4.

6. The purified antagonist according to claim 2, in which said immunoglobulin domain is a light chain of IgG.

7. The purified antagonist according to claim 6, in which said light chain is the kappa chain of IgG.

8. The purified antagonist according to claim 6, in which said light chain is the lambda chain of IgG.

9. A purified antagonist of interleukin-1 comprising:
a) the extracellular domain but not the transmembrane and cytoplasmic domains of the specificity determining component of the interleukin-1 receptor; and
b) the extracellular domain but not the transmembrane and cytoplasmic domains of the signal transducing component of the interleukin-1 receptor;
wherein the antagonist is capable of binding interleukin-1 to form a nonfunctional complex.

10. A purified antagonist of interleukin-2 comprising:
a) the extracellular domain but not the transmembrane and cytoplasmic domains of the specificity determining component of the interleukin-2 receptor; and
b) the extracellular domain but not the transmembrane and cytoplasmic domains of the signal transducing component of the interleukin-2 receptor;
wherein the antagonist is capable of binding interleukin-2 to form a nonfunctional complex.

11. A purified antagonist of interleukin-3 comprising:
a) the extracellular domain but not the transmembrane and cytoplasmic domains of the specificity determining component of the interleukin-3 receptor; and
b) the extracellular domain but not the transmembrane and cytoplasmic domains of the signal transducing component of the interleukin-3 receptor;
wherein the antagonist is capable of binding interleukin-3 to form a nonfunctional complex.

12. A purified antagonist of interleukin-4 comprising:
a) the extracellular domain but not the transmembrane and cytoplasmic domains of the specificity determining component of the interleukin-4 receptor; and
b) the extracellular domain but not the transmembrane and cytoplasmic domains of the signal transducing component of the interleukin-4 receptor;
wherein the antagonist is capable of binding interleukin-4 to form a nonfunctional complex.

13. A purified antagonist of interleukin-5 comprising:
   a) the extracellular domain but not the transmembrane and cytoplasmic domains of the specificity determining component of the interleukin-5 receptor; and
   b) the extracellular domain but not the transmembrane and cytoplasmic domains of the signal transducing component of the interleukin-5 receptor;

wherein the antagonist is capable of binding interleukin-5 to form a nonfunctional complex.

14. A purified antagonist of interleukin-15 comprising:
   a) the extracellular domain but not the transmembrane and cytoplasmic domains of the specificity determining component of the interleukin-15 receptor; and
   b) the extracellular domain but not the transmembrane and cytoplasmic domains of the signal transducing component of the interleukin-15 receptor;

wherein the antagonist is capable of binding interleukin-15 to form a nonfunctional complex.

15. A purified antagonist of granulocyte macrophage colony stimulating factor comprising:
   a) the extracellular domain but not the transmembrane and cytoplasmic domains of the specificity determining component of the granulocyte macrophage colony stimulating factor receptor; and
   b) the extracellular domain but not the transmembrane and cytoplasmic domains of the signal transducing component of the granulocyte macrophage colony stimulating factor receptor;

wherein the antagonist is capable of binding granulocyte macrophage colony stimulating factor to form a nonfunctional complex.

16. A purified antagonist of gamma-interferon comprising:
   a) the extracellular domain but not the transmembrane and cytoplasmic domains of the specificity determining component of the gamma-interferon receptor; and
   b) the extracellular domain but not the transmembrane and cytoplasmic domains of the signal transducing component of the gamma-interferon receptor;

wherein the antagonist is capable of binding gamma-interferon to form a nonfunctional complex.

17. A purified antagonist of Transforming Growth Factor-Beta comprising:
   a) the extracellular domain but not the transmembrane and cytoplasmic domains of the specificity determining component of the Transforming Growth Factor-Beta receptor; and
   b) the extracellular domain but not the transmembrane and cytoplasmic domains of the signal transducing component of the Transforming Growth Factor-Beta receptor;

wherein the antagonist is capable of binding Transforming Growth Factor-Beta to form a nonfunctional complex.

* * * * *